(12) United States Patent
Chang et al.

(10) Patent No.: US 6,420,523 B1
(45) Date of Patent: *Jul. 16, 2002

(54) BACULOVIRUS PRODUCED PLASMODIUM FALCIPARUM VACCINE

(75) Inventors: Sandra Chang; George S. N. Hui, both of Honolulu, HI (US); Philip J. Barr, Berkeley; Helen Gibson, Oakland, both of CA (US)

(73) Assignee: University of Hawaii, Honolulu, HI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/195,705

(22) Filed: Feb. 14, 1994

Related U.S. Application Data

(62) Division of application No. 07/867,768, filed on Apr. 13, 1992, now abandoned.

(51) Int. Cl.[7] .................. C07K 1/00; A61K 39/015; A61K 39/00

(52) U.S. Cl. ............. 530/350; 424/268.1; 424/272.1; 424/185.1; 424/191.1

(58) Field of Search ................. 424/268.1, 272.1, 424/185.1, 191.1; 530/350, 395

(56) References Cited

U.S. PATENT DOCUMENTS 4,745,051 A  5/1988  Smith et al. ................. 435/68

FOREIGN PATENT DOCUMENTS

EP          0329257    * 8/1989

OTHER PUBLICATIONS

Smilek, D et al., PNAS 88:9633–37, A single amino acid change in myelin basic protein peptide confers the capacity to prevent rather thatn induce EAE, Nov. 1991.*

Holder, A. A. et al., Parasite Immunology 10:607–617 (1988), Immunization against *Plasmodium falciparum* with recombinant polypeptides produced in *Escherichia coli*.

Tanabe, K. et al., J. Mol. Biology 195:273–287 (1987), Allelic dimorphism in a surface antigen gene of the malaria parasite *Plasmodium falciparum*.

Cheung et al. "Immunization with synthetic peptides of a *Plasmodium falciparum* surface antigen induces antimerozite antibodies, " Proc. Natl, Acad, Sci. USA 83:8328 (1986).

Hall et al. "Major surface antigen gene of a human malaria parasite cloned and expressed in bacteria," Nature 311:379 (1984).

Herrera et al. "Immunization of Aotus monkeys with *Plasmodium falciparum* blood–stage recombinant proteins, " Proc. Natl. Acad. Sci. USA 87:4017 (1990).

Herrera et al. "Conserved Polypeptides of *Plasmodium* Falciparum as Malaria Vaccine Candidates ?", Acta Leidensia, 60(1): 107–110 (1991).

(List continued on next page.)

Primary Examiner—Mark Navarro
Assistant Examiner—Iesha Fields
(74) Attorney, Agent, or Firm—Flehr Hohbach Test Albritton & Herbert LLP; Todd A. Lorenz, Esq.; Richard F. Trecartin, Esq.

(57) ABSTRACT

The present invention provides compositions of matter comprising a polypeptide expressed from insect cells harboring a baculovirus vector the encodes the polypeptide, wherein the polypeptide comprises amino acid sequences derived from the p42 fragment of the *Plasmodium falciparum* gp 195 protein or derivatives thereof. Such compositions of matter find use for example for inducing the production of anti-p42 antibodies both in vivo and in vitro.

13 Claims, 8 Drawing Sheets

OTHER PUBLICATIONS

Holder et al. "Immunization against boold–stage rodent malaria using purified parasite antigens," Nature 294:361 (1981).

Hui et al. "Serum from Pf195 protected Aotus Monkeys Inhibit *Plasmodium falciparum* growth in Vitro," Exp. Parasitol. 64–519 (1987).

Knapp et al. "A histidin alanine rich recombinant antigen protects aotus monkeys from P. Falciparum infection," Behring Inst. Mitt. 82:349 (1988).

Lew et al. "A protective monoclonal antibody recognizes a linear epitope in the precursor to the major merozite antigens of *Plasmodium chabaudi adami*," Proc. Natl. Acad. Sci. USA 86:3768 (1989).

Majarian et al. "Passive Immunization against Murine Malaria with an IgG3 Monoclonal Antibody," J. Immunol. 132:3131 (1984).

Patarroyo et al. "A synthetic vaccine protects humans against challenge with asexual blood stages of *Plasmodium falciparum* malaria," Mature 332:158 (1988).

Patarroyo et al. "Protective Synthetic Peptides against Experimental *Plasmodium falciparum* –induced Malaria," Vaccines 87 (Brown, Chanock, Lerner, ed.) Cold Spring Harbor Laboratory Press, CSH, NY. 117–124 (1987).

Patarroyo et al. "Induction of protective immunity against experimental infection with malaria using synthetic peptides," Nature 328:629 (1987).

Perrin et al. "Antimalarial Immunity in Saimiri Monkeys," J. Exp. Med. 160:441 (1984).

Ruebush et al. "Immunization of Oql Monkeys with a Combination of *Plasmodium Falciparum* Asexual Blood–Stage Synthetic Peptide Antigens," Am. J. Trop. Med. Hyg. 43:355–366 (1990).

Rodriquez et al. Studies In Owl Monkeys Leading to the Development of a Synthetic Vaccine Against the Asexual Blood Stages of *Plasmodium Falciparum*, Am. J. Trop. Med. Hyg. 43:339 (1990).

Siddiqui et al. "Merozoite surface coat presursor protein completely protects Aotus monkeys against *Plasmodium falciparum* malaria," 1987. Proc. Natl. Acad. Sci. USA 84:3014.

Odink KG. et al. "Expression of cloned cDNA for a major surface antigen of Plasmodium falciparum merozoite," FEBS Lett. (1984) 108–12.

Murphy et al., "Expression of hybrid malaria antigens in insect cells and their engineering for correct folding and secretion,"Parasitology, 100:177–183 (100).

Holder et al., "A hybrid gene to express protein epitopes from both sporozoite and merozoite surface antigens of *Plasmodium falciparum*," Parisitology, 97:373–382 (1988).

Schwarz et al, "Structural Diversity of the Major Surface Antigen of *Plasmosium falciparum* Merozoite,"Molecular and Cellular Biology, 6(3);964–968 (1986).

Holder et al., "Primary Structure of the Precursor to the three major surface antigens of *Plasmodium falciparum* merozoite,"Nature, 317–270–273 (1985).

Holder et al., "Processing of the presursor to the major merozoite surface antigens of *Plasmodium falciparum*," Parisology, 94:199–208 (1987).

Tanabe, et al., "Allelic Dimorphism in a Surface Antigen Gene of the Malaria Parasite *Plasmodium falciparum*," J. Mol. Biol., 195:273–287 (1987).

Holder et al., "Immunization against *Plasmodium falciparum* with recombinant polypeptides produced in *Escherichia coli*," Parastic Immunology, 10:607–617 (1988).

* cited by examiner

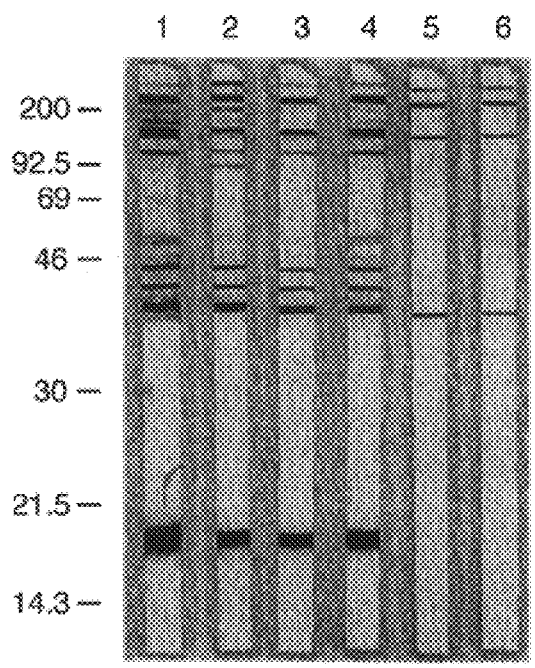
FIG._3A
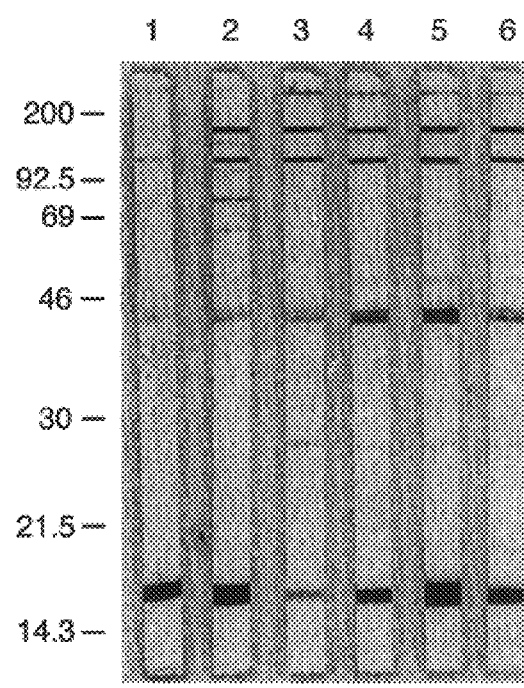
FIG._3B
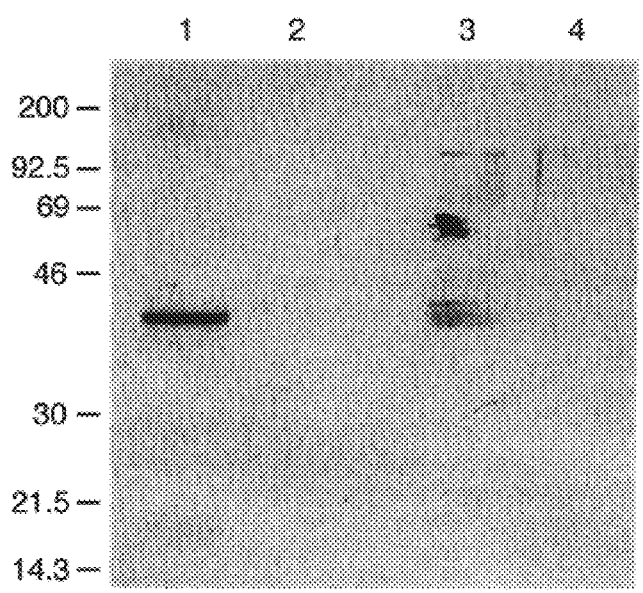
FIG._3C

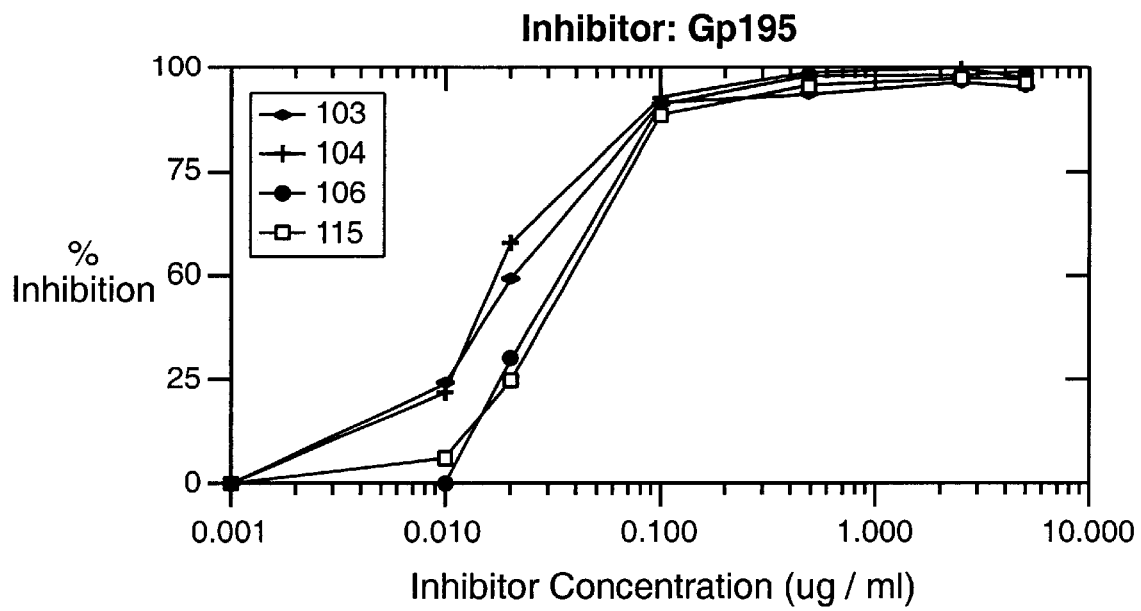
FIG._4A
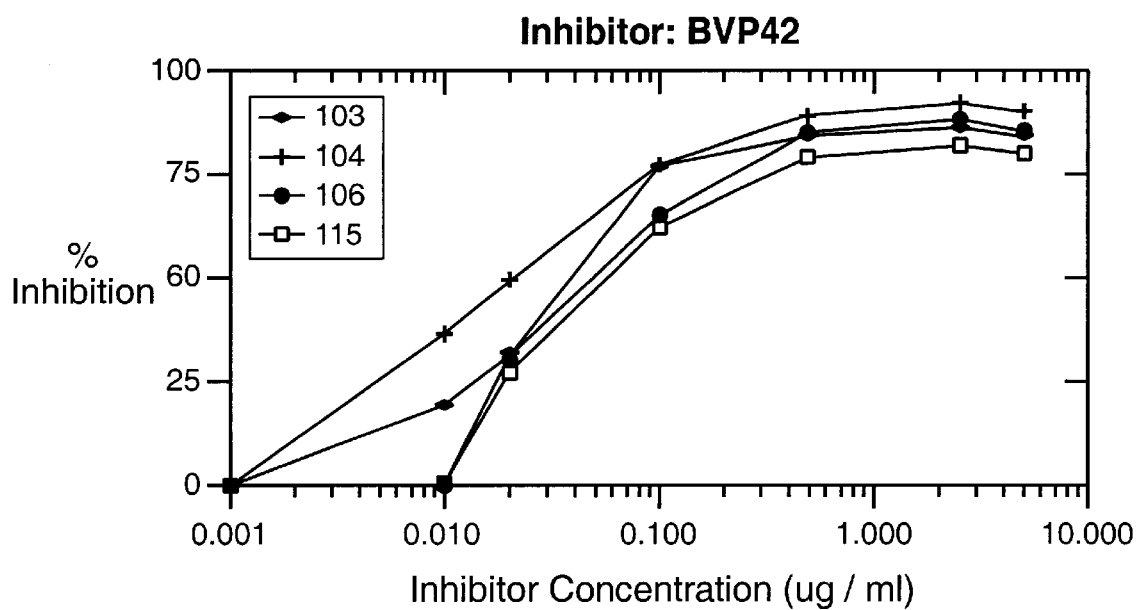
FIG._4B

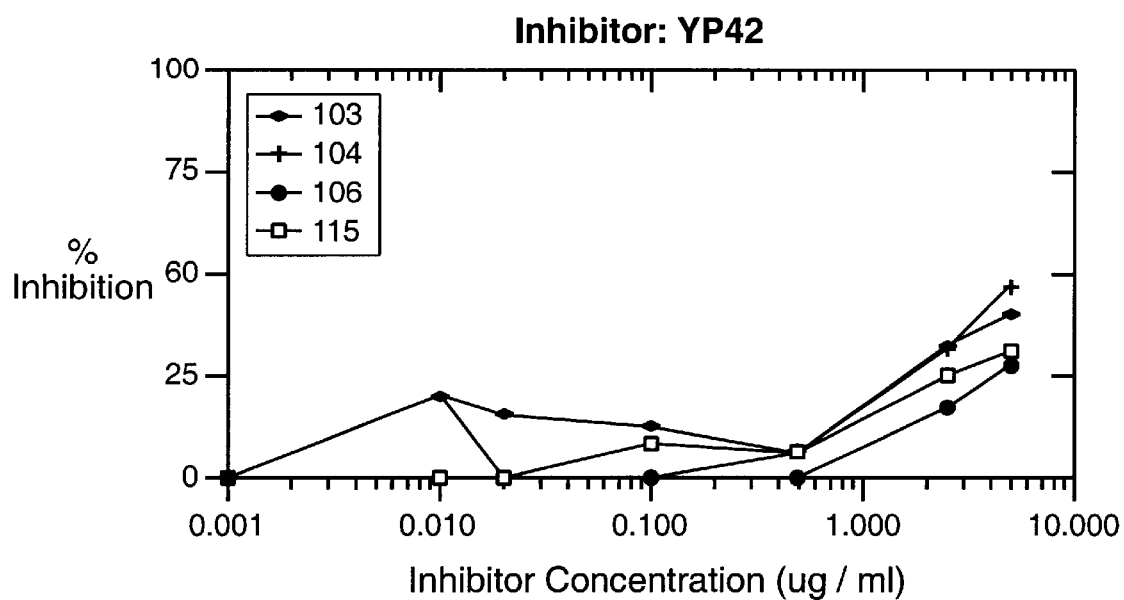
FIG._4C
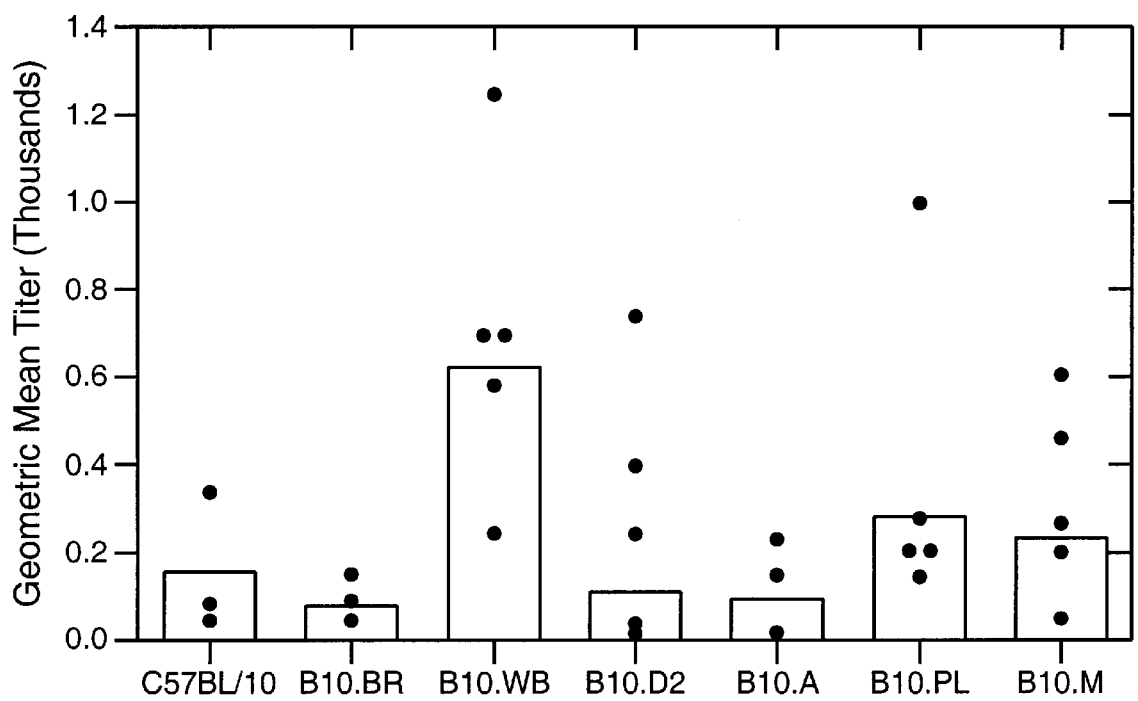
FIG._5

```
FUP  AISVT.MDNILSGFENEYDVIYLKPLAGVYRSLKKQIEKNIFTPNLNLNDILNSRLKKRKYFLDVLESDLM           1402
MAD                                                                                   1377
WEL  VTTSVI          KI      E L                    L N VM     V VK          FN  EN KN   I  1384
 K1  VTPSVIH         KI      E L                    L N VM     V VK          PFN EN KN   I  1325

FUP  QFKHISSNEYIIEDSFKLLNSEQKNTLLKSYKYIKESVENDIKFAQEGISYYEKVLAKYKDDLESIKKVIK          1473
MAD                                  I                                                1448
WEL  PY DLT SN VVK PY F   K KRDKF S  N    D IDT  N  NDVLG  KILSE      S   D      Y N  1405
 K1  PY DLT SN VVK PY F   K KRDKF S  N    D IDT  N  NDVLG  KILSE      S   D      Y N  1396

FUP  EEKEKFPSSPPTTPPSPAKTDEQKKESKFLPFLTNIETLYNNLVNKIDDYLINLKAKINDCNVEKDEAHVK          1544
MAD                                        ◇                                          1519
WEL  ........... K GENE Y               N           KTVND       LFV H E   VLNYTY SNVE  1456
 K1  ........... K GENE Y               N           KTVND       LFV H E   VLNYTY SNVE  1447

FUP  ITKLSDLKAIDDKIDLFKNHNDFEAIKKLINDDTKKDMLGKLLSTGLV.QNFPNTIISKLIEGKFQDML.N           1613
MAD                       T                                       I                    1588
WEL  KE NY  T Q  LAD   KN N VG AD ST YNHNNL T F       M FE LLKSVL N LDW LARYVKH        1527
 K1  KE IY  T Q  LAD   KN N VG AD ST YNHNNL T F       M FE LLKS  L N LDW LARYVKH       1518

FUP  ISQHQCVKKQCPENSGCFRHLDEREECKCLLNYKQEGDKCVENPNPTCNENNGGCDADAKCTEEDSGSNGK           1684
MAD                                   E                                T              1659
WEL  FTTPMRK TMIQQS                              S                                 SR  1598
 K1  FTTPMRK TMIQQ                                                                     1589

FUP  KITCECTKPDSYPLFDGIFCSSSNFLGISFLLIMLILYSFI                                         1726
MAD                    ↑                                                              1701
WEL                                                                                    1640
 K1      C      SMV                                                                   1631

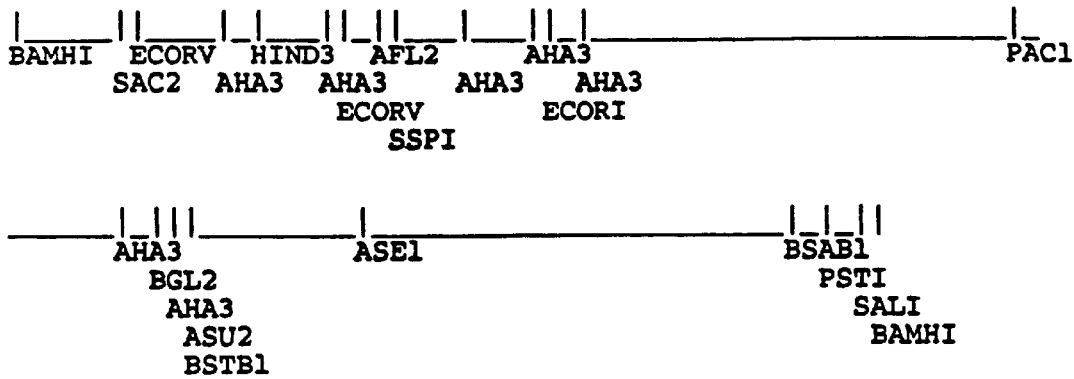

```
          |____||____|_||_||____|__||_|                              |_
          BAMHI  ECORV HIND3 AFL2    AHA3                             PAC1
          SAC2   AHA3  AHA3  AHA3    AHA3
                 ECORV       AHA3    ECORI
                 SSPI

_____|_|||_____|_____|_|_||
               AHA3                ASE1                BSAB1
               BGL2                                    PSTI
               AHA3                                    SALI
               ASU2                                    BAMHI
               BSTB1
```

```
                  MetTrpSerTrpLysCysLeuLeuPheTrpAlaValLeuValThrAla
  1   GGATCCACTGGGATGTGGAGCTGGAAGTGCCTCCTCTTCTGGGCTGTCCTGGTCACAGCC
      CCTAGGTGACCCTACACCTCGACCTTCACGGAGGAGAAGACCCGACAGGACCAGTGTCGG

1 BAMHI,
                       V
      ThrLeuCysThrAlaAlaIleSerValThrMetAspAsnIleLeuSerGlyPheGluAsn
 61   ACACTCTGCACCGCGGCGATATCTGTCACAATGGATAATATCCTCTCAGGATTTGAAAAT
      TGTGAGACGTGGCGCCGCTATAGACAGTGTTACCTATTATAGGAGAGTCCTAAACTTTTA

71 SAC2, 78 ECORV,

GluTyrAspValIleTyrLeuLysProLeuAlaGlyValTyrArgSerLeuLysLysGln
121   GAATATGATGTTATATATTTAAAACCTTTAGCTGGAGTATATAGAAGCTTAAAAAAACAA
      CTTATACTACAATATATAAATTTTGGAAATCGACCTCATATATCTTCGAATTTTTTGTT

138 AHA3, 165 HIND3,

IleGluLysAsnIlePheThrPheAsnLeuAsnLeuAsnAspIleLeuAsnSerArgLeu
181   ATTGAAAAAAACATTTTTACATTTAATTTAAATTTGAACGATATCTTAAATTCACGTCTT
      TAACTTTTTTTGTAAAAATGTAAATTAAATTTAAACTTGCTATAGAATTTAAGTGCAGAA

207 AHA3, 220 ECORV, 238 AFL2,

LysLysArgLysTyrPheLeuAspValLeuGluSerAspLeuMetGlnPheLysHisIle
241   AAGAAACGAAAATATTTCTTAGATGTATTAGAATCTGATTTAATGCAATTTAAACATATA
      TTCTTTGCTTTTATAAAGAATCTACATAATCTTAGACTAAATTACGTTAAATTTGTATAT

251 SSPI, 289 AHA3,

SerSerAsnGluTyrIleIleGluAspSerPheLysLeuLeuAsnSerGluGlnLysAsn
```

FIG._7A

```
301  TCCTCAAATGAATACATTATTGAAGATTCATTTAAATTATTGAATTCAGAACAAAAAAAC
     AGGAGTTTACTTATGTAATAACTTCTAAGTAAATTTAATAACTTAAGTCTTGTTTTTTG
```

331 AHA3, 342 ECORI,

```
         ThrLeuLeuLysSerTyrLysTyrIleLysGluSerValGluAsnAspIleLysPheAla
361  ACACTTTTAAAAAGTTACAAATATATAAAAGAATCAGTAGAAAATGATATTAAATTTGCA
     TGTGAAAATTTTTCAATGTTTATATATTTTCTTAGTCATCTTTTACTATAATTTAAACGT
```

366 AHA3,

```
         GlnGluGlyIleSerTyrTyrGluLysValLeuAlaLysTyrLysAspAspLeuGluSer
421  CAGGAAGGTATAAGTTATTATGAAAAGGTTTTAGCGAAATATAAGGATGATTTAGAATCA
     GTCCTTCCATATTCAATAATACTTTTCCAAAATCGCTTTATATTCCTACTAAATCTTAGT
```

```
         IleLysLysValIleLysGluGluLysGluLysPheProSerSerProProThrThrPro
481  ATTAAAAAAGTTATCAAAGAAGAAAAGGAGAAGTTCCCATCATCACCACCAACAACACCT
     TAATTTTTTCAATAGTTTCTTCTTTTCCTCTTCAAGGGTAGTAGTGGTGGTTGTTGTGGA
```

```
         ProSerProAlaLysThrAspGluGlnLysLysGluSerLysPheLeuProPheLeuThr
541  CCGTCACCAGCAAAAACAGACGAACAAAAGAAGGAAAGTAAGTTCCTTCCATTTTTAACA
     GGCAGTGGTCGTTTTTGTCTGCTTGTTTTCTTCCTTTCATTCAAGGAAGGTAAAAATTGT
```

```
         AsnIleGluThrLeuTyrAsnAsnLeuValAsnLysIleAspAspTyrLeuIleAsnLeu
601  AACATTGAGACCTTATACAATAACTTAGTTAATAAAATTGACGATTACTTAATTAACTTA
     TTGTAACTCTGGAATATGTTATTGAATCAATTATTTTAACTGCTAATGAATTAATTGAAT
```

649 PAC1,

```
         LysAlaLysIleAsnAspCysAsnValGluLysAspGluAlaHisValLysIleThrLys
661  AAGGCAAAGATTAACGATTGTAATGTTGAAAAAGATGAAGCACATGTTAAAATAACTAAA
     TTCCGTTTCTAATTGCTAACATTACAACTTTTTCTACTTCGTGTACAATTTTATTGATTT
```

```
         LeuSerAspLeuLysAlaIleAspAspLysIleAspLeuPheLysAsnHisAsnAspPhe
721  CTTAGTGATTTAAAAGCAATTGATGACAAAATAGATCTTTTTAAAAACCATAACGACTTC
     GAATCACTAAATTTTCGTTAACTACTGTTTTATCTAGAAAAATTTTTGGTATTGCTGAAG
```

729 AHA3, 753 BGL2, 760 AHA3, 778 ASU2 BSTB1,

```
         GluAlaIleLysLysLeuIleAsnAspAspThrLysLysAspMetLeuGlyLysLeuLeu
781  GAAGCAATTAAAAAATTGATAAATGATGATACGAAAAAGATATGCTTGGCAAATTACTT
     CTTCGTTAATTTTTTAACTATTTACTACTATGCTTTTTCTATACGAACCGTTTAATGAA
```

```
         SerThrGlyLeuValGlnAsnPheProAsnThrIleIleSerLysLeuIleGluGlyLys
841  AGTACAGGATTAGTTCAAAATTTTCCTAATACAATAATATCAAAATTAATTGAAGGAAAA
     TCATGTCCTAATCAAGTTTTAAAAGGATTATGTTATTATAGTTTTAATTAACTTCCTTTT
```

885 ASE1,

```
         PheGlnAspMetLeuAsnIleSerGlnHisGlnCysValLysLysGlnCysProGluAsn
901  TTCCAAGATATGTTAAACATTTCACAACACCAATGCGTAAAAAAACAATGTCCAGAAAAT
     AAGGTTCTATACAATTTGTAAAGTGTTGTGGTTACGCATTTTTTTGTTACAGGTCTTTTA
```

```
         SerGlyCysPheArgHisLeuAspGluArgGluGluCysLysCysLeuLeuAsnTyrLys
961  TCTGGATGTTTCAGACATTTAGATGAAAGAGAAGAATGTAAATGTTTATTAAATTACAAA
     AGACCTACAAAGTCTGTAAATCTACTTTCTCTTCTTACATTTACAAATAATTTAATGTTT
```

FIG._7B

```
         GlnGluGlyAspLysCysValGluAsnProAsnProThrCysAsnGluAsnAsnGlyGly
1021     CAAGAAGGTGATAAATGTGTTGAAAATCCAAATCCTACTTGTAACGAAAATAATGGTGGA
         GTTCTTCCACTATTTACACAACTTTTAGGTTTAGGATGAACATTGCTTTTATTACCACCT

CysAspAlaAspAlaLysCysThrGluGluAspSerGlySerAsnGlyLysLysIleThr
1081     TGTGATGCAGATGCCAAATGTACCGAAGAAGATTCAGGTAGCAACGGAAAGAAAATCACA
         ACACTACGTCTACGGTTTACATGGCTTCTTCTAAGTCCATCGTTGCCTTTCTTTTAGTGT

CysGluCysThrLysProAspSerTyrProLeuPheAspGlyIlePheCysSerAM AM
1141     TGTGAATGTACTAAACCTGATTCTTATCCACTTTTCGATGGTATTTTCTGCAGTTAGTAG
         ACACTTACATGATTTGGACTAAGAATAGGTGAAAAGCTACCATAAAAGACGTCAATCATC

1159 BSAB1, 1188 PSTI, 1200 SALI,

1201     TCGACCCTTGGAAGGATCC
         AGCTGGGAACCTTCCTAGG

1214 BAMHI,

BACULOVIRUS PRODUCED PLASMODIUM FALCIPARUM VACCINE

This application is a divisional of Ser. No. 07/867,768, filed Apr. 13, 1992, now abandoned.

This invention was made with Government support under Contract DPE0453A00901500 of the Agency for International Development. The Government has certain rights in this invention.

FIELD OF THE INVENTION

This invention is in the field of recombinant *Plasmodium falciparum* polypeptides and vaccines.

BACKGROUND OF THE INVENTION

The major merozoite surface protein of Plasmodium species has been shown to be a target of varying degrees of protective immunity against the asexual blood stages in rodent and human malarias.

For example, vaccination of mice with purified P230, the major merozoite surface protein of the rodent malaria *Plasmodium yoelii*, has resulted in reduced parasitemias in comparison to controls upon intravenous challenge with a lethal dose of parasitized erythrocytes (1). Mice have also been protected against *P. yoelii* by passive transfer of a monoclonal antibody specific for P230 (2) and against (rodent malaria) *Plasmodium chabaudi adami* challenge by passive immunization with a monoclonal antibody specific for the homologous 250-kDa molecule of this Plasmodium species (3). The ability to confer resistance to parasite challenge by passive transfer of antibodies suggests that antibody-mediated mechanisms play an important role in antigen-specific immunity to malaria.

Despite these findings, however, no commercially viable vaccine has been developed against the major merozoite surface antigen of the major human malaria pathogen, *Plasmodium falciparum.*

For example, using naturally derived materials, such as the precursor of the major merozoite surface protein alone (gp195: 195-200,000 Da molecular species), gp195 mixed with certain of its natural processing fragments, or a natural processing fragment by a itself partial protection against *Plasmodium falciparum* infection has been achieved by some researchers (4,5,6). An effective vaccine against *Plasmodium falciparum* should not convey merely partial protection, i.e. a partial lowering of parasitemia, since even low parasite mias of this organism cause serious illness. A commercially useful vaccine should substantially eliminate parasitemia.

In one instance, substantially complete protection using natural materials against *Plasmodium falciparum* challenge has been achieved in Aotus monkeys, in particular by the use of a mixture of gp195 and some of its natural processing fragments obtained by affinity purification using a monoclonal antibody, designated Mab 5.2 (7). In follow on experiments using Mab 5.2 affinity purified, parasite gp195, a correlation was found between protection against infection with *Plasmodium falciparum* and the ability of serum antibodies to strongly inhibit parasite growth in vitro. In particular, monkeys and rabbits hyperimmunized with Mab 5.2 affinity purified parasite gp195 in complete Freund's adjuvant produced antibodies that inhibited in vitro parasite growth (8).

The difficulty in developing an effective naturally derived vaccine, however, has been compounded with the difficulty in developing an effective recombinant or synthetic vaccine. Recombinant or synthetic vaccines are desirable for several reasons. They have the potential to focus immune response on the most effective portion of gp195, an important advantage since there may be decoy determinants in gp195 which prevent the most effective response. Also, more homogeneous preparations are possible using recombinant techniques than in preparations of naturally derived products. In addition, recombinant and synthetic based vaccines avoid the potential contamination of naturally derived gp195 with pathogens from its human source.

Although a number of investigators have designed and tested gp195-based synthetic peptides and recombinant products as vaccine antigens no strongly protective vaccine has resulted. Thus, synthetic peptides corresponding to various segments of the N-terminal 83 kDa processing fragment of gp195 induced antibodies in rabbits which displayed only a low level of crossreactivity with asexual blood stage parasites (9). One of these synthetic peptides, corresponding to a non-repetitive, conserved sequence, partially protected Saimiri monkeys against *Plasmodium falciparum* challenge (9). In a vaccination study in Aotus monkeys using an 83 kDa processing fragment-based recombinant polypeptide produced in *E. coli* there was no significant difference between the course of infection of control animals and animals immunized with the recombinant polypeptide (in addition, very low levels of antibodies cross-reactive with native gp195 by immunofluorescence were induced) (10). A bacterial recombinant polypeptide based on a fusion of two conserved regions located towards the amino terminus and center of the gp195 molecule induced only low IFA titers when used to immunize Aotus monkeys (11) and two out of five immunized animals were partially protected.

Holder et al. studied two recombinant polypeptides which corresponded to portions of the 42 kDa C-terminal processing fragment of gp195 (p42) fused to trp E and β-galactosidase carrier sequences, respectively (12). While immunized animals produced high antibody titers against the carrier portion of the recombinant polypeptides, much lower titers were detected against the gp195 antigen. Some of the Aotus monkeys immunized with both of these recombinant polypeptides were partially protected against parasite challenge.

Murphy et al. have attempted to recombinantly produce portions of the p42 antigen of the Wellcome isolate of gp195 in insect host cells. (Gp195 is believed to exist in at least two allelic forms, of which the Wellcome isolate ("Wellcome allele") and the MAD isolate ("MAD allele") are representative (13)). While Murphy et al. reported producing a product which folded in a similar manner to the natural antigen, they did not report obtaining a purified polypeptide (only multiply banded antigens speculated to have resulted from post-translational processing or degradation). No follow-up studies have been reported using any materials obtained.

A mixture of three synthetic peptides, one peptide from the 83 kDa processing fragment of gp195 and two non-gp195 malaria peptides, partially to completely protected monkeys against parasite challenge; a hybrid synthetic polymer including the sequences of the three synthetic peptides in addition to a circumsporozoite region was reported to provide a delay or suppression of parasitemias (14, 15, 16). Field trials of this hybrid are under way. It is unclear whether any gp1 95 epitopes in the mixture or hybrid resulted in any protection. In addition there have been two studies reported which were unable to duplicate the prior results obtained using the peptide mixture (17) or the hybrid peptide multimer (18).

Thus, there has been no gp195-based recombinant or synthetic vaccine antigen which has been shown sufficiently effective against *Plasmodium falciparum* challenge.

SUMMARY OF THE INVENTION

The present invention relates to a vaccine made with baculovirus produced p42 antigen (BVp42), or an effective immunogenic part thereof, which provides strong protection against *Plasmodium falciparum* infection. In addition, BVp42 is capable of inducing antibodies that are extensively crossreactive with different parasite strains. The invention also relates to a method of producing BVp42 based antigens without cleavage or degradation by infecting an insect host cell with a recombinant baculovirus vector that contains DNA encoding a p42 amino acid sequence that is characteristic of the MAD-allele. The DNA sequence is operably linked to a baculovirus polyhedron promoter.

BRIEF DESCRIPTION OF THE DRAWINGS

FIGS. 1A–1B are schematic representations of a baculovirus p42 gene construct. In FIG. 1A the structure of baculovirus p42 consists of the flg5 leader sequence (flg$_L$, solid box) fused to the p42 coding region from amino acids Ala$_{1333}$ to Ser$_{1705}$. In FIG. 1B synthetic DNA (solid boxes) encodes the flg5 leader and 5' region of p42 as a BamH1 (B)/HindIII fragment. A synthetic Pst1(P)/Sal1(L) linker encodes the termination codon (solid box) at the 3' end of the construct. The HindIII/Pst1 fragment was derived from cloned parasite DNA.

FIGS. 2A–B depict silver stains (lane 1) and immunoblots (lane 2) of BVp42 (FIG. 2A) and Yp42 (FIG. 2B) electrophoresed in a 10% SDS-polyacrylamide gel. Immunoblots were reacted with rabbit anti-parasite gp195.

FIGS. 3A–C show immunoblots of purified parasite gp195 electrophoresed under nonreducing (FIG. 3A) or reducing (FIG. 3B) conditions and reacted with anti-gp195 monoclonal antibody 5.2 (lane 1); rabbit anti-parasite gp195 (lane 2); rabbit anti-BVp42; (#131, lane 3 and #132, lane 4); rabbit anti-Yp42 (#93, lane 5 and #96, lane 6). FIG.3C shows immunoblots of BVp42 (lane 1, non-reduced; lane 2, reduced) and Yp42 (lane 3, non-reduced; lane 4, reduced) reacted with monoclonal antibody 5.2.

FIGS. 4A–C are graphs depicting a competition ELISA using purified, parasite gp195 coated plates and BVp42 and gp195 inhibitors.

FIG. 5 is a graph showing ELISA titers against a BVp42 antigen of anti-parasite gp195 sera of congenic mice.

FIG. 6 shows amino acid sequences of FUP isolate p42 (SEQ ID NO: 2) and of the corresponding MAD, K1 and Wellcome strains (SEQ ID NOS: 3–5). Amino acids shown in the MAD, K1 and Wellcome strains (SEQ ID NOS: 3–5) are those that are different from those of the FUP strain (SEQ ID NO: 2). Deletions are shown by a period. Also indicated are the sites for post-translational modification (conserved potential N-glycosylation sites are shown as filled diamonds and non-conserved sites by open diamonds; conserved cysteines are shown by filled circles and non-conserved by open circles) and the beginning of the putative transmembrane region is indicated by the arrow. Number of amino acids is according to Chang et al. (33)

FIGS. 7A–C show the sequence of a DNA construct (SEQ ID NO: 1) described in Example 1. The construct codes for a flg5 leader polypeptide adjacent to amino acids 1333 to 1705 of the FUP isolate gp195 (SEQ ID NO: 2), as those amino acids are numbered in FIG. 6.

DETAILED DESCRIPTION OF THE INVENTION

Figure 1B:
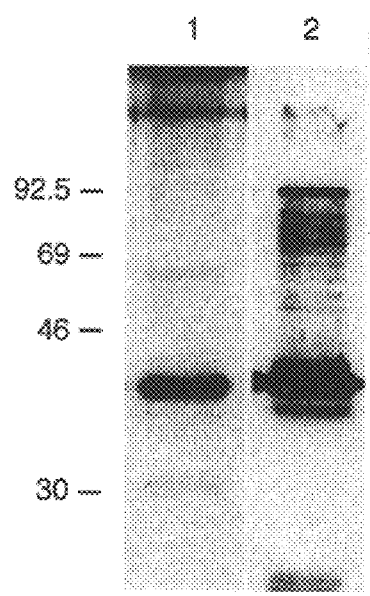

BVp42 antigen of *Plasmodium falciparum* gp195 induces antibodies that strongly, if not substantially completely, inhibit parasite growth and forms the basis of a vaccine. The antibodies are extensively crossreactive with different parasite strains, and have been found to strongly or completely inhibit parasite growth of heterologous parasites to the same degree as homologous parasites. BVp42, as described herein, is a variant of the natural p42 processing fragment of gp195 that has been recombinantly expressed in insect cells using a baculovirus expression vector. The term BVp42 is used herein to refer to the p42 amino acid sequence as characteristically produced in insect cells, in particular in sf9 insect cells. The amino acid sequence of p42 of different isolates is shown in FIG. 6, i.e. amino acids nos. 1333 to 1726 in the FUP isolate (SEQ ID NO:2) , 1308 to 1701 in the (SEQ ID NO: 4); 1264 to 1640 in the Wellcome isolate, and 1255 to 1631 in the K1 isolate (SEQ ID NO: 3) (the numbers refer to the amino acids of the precursor molecule, gp195). The term p42 refers to the corresponding sequences in other isolates as well. A preferred embodiment of the invention includes only the amino acids Ala$_{1333}$ to Ser$_{1705}$ of the FUP isolate (SEQ ID NO: 2) (33), or the corresponding amino acids of other isolates (e.g. Ala$_{1308}$, to Ser$_{1680}$ of the MAD isolate (SEQ ID NO:4) (20), Ala$_{1264}$ to Ser$_{1619}$ of the Wellcome isolate (SEQ ID NO: 5) (19), Ala$_{1255}$ to Ser$_{1610}$ of the K1 isolate (SEQ ID NO:5) (20)). (The numbering of these amino acids also corresponds to that shown in FIG. 6.) The antigen of this embodiment deletes the anchor sequence at the C-terminus of p42, allowing easier recovery of the product because it is secreted from the host cells.

The amino acid sequences of isolates bearing the same designation may vary somewhat, as may the DNA sequences coding for those isolates. Similarly, the numberings of the amino acid and DNA sequences in other publications may differ from the numberings shown herein. A particular amino acid and DNA sequence of a FUP isolate corresponding to amino acids Ala$_{1333}$ to Ser$_{1705}$ (SEQ ID NO:2)(as shown in FIG. 6) is described in the examples below and has the sequences shown in FIG. 7 (SEQ ID NO:1).

In another aspect of the invention, as noted above, we have found that when a p42 amino acid sequence is expressed in insect cells, a pure product can be obtained without degradation or cleavage if DNA coding for a MAD allele sequence is employed. An amino acid sequence of the p42 antigen is considered be of the MAD allele if it corresponds to the parts of gp1 95 of the MAD *Plasmodium falciparum* isolate which are dimorphic as compared with the amino acid sequences of the Wellcome and K1 isolates (13). For example, gp195 of the FUP isolate is of the MAD allele (23, 33) (FUP isolate p42 amino acid sequence is as well).

The method for producing BVp42 according to this aspect of the invention involves infecting an insect cell host with a recombinant is baculovirus vector, that vector containing DNA coding for a p42 amino acid sequence of surface protein gp195 of the *Plasmodium falciparum* MAD allele, operably linked to a baculovirus polyhedron promoter. Production of BVp42 with the sequence of the MAD allele, preferably of the FUP isolate sequence, results in pure, undegraded antigen.

A high level of inhibition of parasite growth is exhibited by anti-BVp42 sera. As noted above, strong inhibition of parasite growth by sera of monkeys vaccinated with Mab 5.2 affinity purified parasite gp1 95 correlates with the ability to induce substantially complete protection against infection.

Without wishing to be bound by any theory of the invention, our results provide new insights into the interpretation of the vaccination study discussed above utilizing parasite gp195 that was affinity purified using Mab 5.2. As shown herein, utilization of this monoclonal antibody (now found by us to be specific for a conformational epitope located within the p42 processing fragment) for affinity purification of parasite gp195 results in an antigen preparation that contains the gp195 precursor but that is also highly enriched for several C-terminal processing fragments, including p42. Based on the analysis of the specificity of anti-parasite gp195 antibodies utilizing the BVp42 polypeptide, a majority of antibodies produced by immunization with Mab 5.2 affinity purified parasite gp195 is specific for the C-terminal p42 processing fragment. The importance of p42 epitopes in immunity is consistent with the strong inhibition of parasite growth obtained with anti-BVp42 sera. There have been reports of several monoclonal antibodies specific for this region which inhibit in vitro parasite growth (21,22). Thus, it is possible that the exceptional level of protection achieved in the previous vaccination study was due to the focusing of the immune response on C-terminal epitopes which appear to serve as targets of functional effects such as the direct inhibition of parasite growth.

A study of the influence of MHC genes on immunological responsiveness to gp195 had found that a variety of congenic mouse strains were capable of producing antibodies against gp1 195 (23). We have detected BVp42-specific antibodies in seven congenic mouse strains immunized with purified, parasite gp195, indicating that individuals of many H-2 haplotypes are capable of recognizing epitopes within the smaller, p42 region of gp195. Thus, BVp42 can likely be used as a vaccine antigen in hosts of diverse genetic makeup.

Techniques known to one skilled in the art for expressing foreign genes in insect host cells can be used to practice the invention. Methodology for expressing polypeptides in insect cells is described, for example, in Summers and Smith (24), Luckow (25), and in U.S. Pat. No. 4,745,051, all hereby incorporated by reference. The techniques are summarized below.

To make BVp42, or an effective immunogenic part thereof, a polyhedron shuttle vector is used to shuttle all or part of the p42 coding sequence into a nuclear polyhedrosis virus. This vector contains the promotor of the polyhedron gene of a nuclear polyhedrosis virus and an available cloning site for the insertion of a selected gene such that the selected gene is under transcriptional control of the polyhedron promotor. Thus, the shuttle vector is engineered to contain the p42 sequence operably linked to a baculovirus polyhedrin promoter.

For example, the p42 sequence can be inserted into a commonly used polyhedron transfer vector, such as pAC373, to produce a recombinant shuttle vector for introducing foreign genes into a nuclear polyhedrosis viruses, such as *Polyhedron californica* nuclear polyhedrosis virus (AcMNPV), resulting in a recombinant viral expression vector capable of expressing the gene encoding for p42 in a host insect cell. pAC373 contains a deletion of the sequence between −8 (8 bases upstream from the polyhedron ATG and approximately 40 bases downstream from the polyhedron transcriptional start site) and the natural BAMH1 sites at nucleotide +171 (26) resulting in a construct which can be used to express full-length gene which contains an internal ATG (N-formyl methionine initiation).

Any p42 coding DNA can be used to make the expression vector. While natural DNA sequences of various *Plasmodium falciparum* isolates (SEQ ID NO: 1) are described in the examples, it is within ordinary skill in the art to vary those sequences. Thus, non-natural DNA sequences, different from the particular ones listed herein, can be used effectively in practicing the invention.

Similarly, non-natural amino acid sequences can be coded for by the DNA used in the transfer vector in order to obtain functional products that obtain the advantages of the invention.

The C-terminus of BVp42 is preferably truncated, as discussed above, to remove the hydrophobic tail sequence (i.e., membrane anchor) to allow for protein secretion. For example, the entire anchor sequence e.g. amino acids 1708–1725 of the FUP isolate (SEQ ID NO:2) and corresponding amino acids of other isolates, can be deleted. An embodiment discussed in the examples below deletes an additional two amino acids at the N-terminus of the anchor sequence.

Thus it is within the scope of the invention to delete portions of the p42 amino acid sequence which do not affect the beneficial result obtained with the BVp42 products exemplified herein.

Transfer of the hybrid DNA to an expression vector is accomplished by transfection of the host insect cell, e.g. sf, with a mixture of both the recombinant transfer plasmid DNA and wild type nuclear polyhedrosis virus (MNPV). The transfected plasmid DNA recombines with the homologous sequences in the wild-type baculovirus genome to produce a viral genome that carries an integrated copy of the foreign gene.

The recombinant expression vector, comprising the hybrid polyhedron-p42 gene incorporated in the MNPV genome is then selected from the mixture of nonrecombinant and recombinant baculoviruses. For example, the supernatant containing the mixture of wild-type and recombinant budded viruses is collected, clarified by centrifugation and used for subsequent plaque assays. The preferred means of selection is by visual screening for the absence of viral occlusion bodies by plaque hybridization with DNA coding for p42, such as described in Kiefer et al. (27).

Expression of the p42 gene is accomplished by infecting susceptible host insect cells, such as sf cells, with the recombinant baculovirus p42-expression vector in an appropriate medium for growth. Propagation of the baculovirus p42-expression vector is achieved in the insect cells through replication and assembly of infectious virus particles.

Various nuclear polyhedrosis viruses can be employed in making expression vectors for use in the invention. Suitable viruses include, but are not limited to, *Polyhedron californica* nuclear polyhedrosis virus (AcMNPV), *Spodoptera frugiperda* nuclear polyhedrosis virus, *Choristoneura fumiferana* nuclear polyhedrosis virus, *Spodoptera littoralis* nuclear polyhedrosis virus, or *trichoplusia ni* nuclear polyhedrosis virus, all known in the art and commonly available.

Suitable insect host cells for use in the invention include, but are not limited to, Sf9 (*Spodoptera frugiperda*), *Spodoptera exiaua, Choristoneura fumiferana, Trichoplusia ni*, and *Spodoptera littoralis*.

The polypeptide may be produced as either a fusion product, such as a heterologous protein containing part baculovirus amino acid sequence fused to *Plasmodium falciparum* sequence, or the product may merely contain a *Plasmodium falciparum* sequence. Methods of making both types of proteins are well known to one skilled in the art.

DNA encoding a leader sequence can be included in the expression vector to facilitate sorting through the endoplasmic reticulum and proper folding of the polypeptide product. For example, flg5 cDNA encoding a leader sequence can be inserted 5' to the p42 coding region using conventional techniques. The flg5 leader is described in Kiefer et al. (27). It is also disclosed in the Genebank and EMBL data bases (accession no. M60485). In addition, the flg5 DNA sequence (SEQ ID NO:1) used in a construct described in the examples below is shown in FIG. 7. The final purified product according to the invention may include a leader sequence, or the sequence may be cleaved during expression. It is believed that the flg5 leader is cleaved during expression.

The many variations in techniques for expressing and isolating BVp42 will be apparent to one skilled in the art.

The BVp42 product can be conventionally purified, such as, in a part, by affinity chromatography with a monoclonal antibody specific for natural p42. Mab 5.2 is one such antibody.

The BVp42 obtained is a variant of naturally occurring p42 that results from characteristic post-translational processing occurring in insect cells, especially sf9 cells. Potential sites for post-translational modifications are shown in FIG. 6.

BVp42 has been found to be highly immunogenic in rabbits. High antibody titers against the immunogen can be obtained which meet or exceed titers of animals immunized with purified parasite gp195. ELISA titers were found similar in assays utilizing plates coated with either purified, parasite gp195 or BVp42. More importantly, high titers were obtained when anti-BVp42 antibodies were reacted with purified, parasite gp195 in an ELISA and in an indirect immunofluorescence assay with schizonts and merozoites. IFA titers obtained after the fourth immunization with BVp42 reached levels exceeding those obtained by immunization with purified, parasite gp195.

Yeast produced p42 (Yp42) consisting of the same p42 sequence (amino acids nos. 1333 to 1705 in the FUP isolate, (SEQ ID NO: 2) was found to be less immunogenic than BVp42, inducing lower antibody titers against the immunogen. In addition, the cross-reactivity of anti-Yp42 antibodies with parasite gp195 in the ELISA was much lower than cross-reactivity of anti BVp42 antibodies. Yp42 also induced much lower IFA titers than BVp42, and statistically insignificant levels of parasite inhibition.

Immunoblotting studies demonstrated that most of the anti-BVp42 and anti-parasite gp195 antibodies produced are specific for disulfide-dependent, conformational epitopes present on the same set of gp195 processing fragments.

An adjuvant should be included with the BVp42 in the vaccine of the invention in order to enhance the immune response. Such adjuvants include Freunds complete adjuvant, B30-MDP, LA-15-PH, (28,29,32) saponin, aluminum hydroxide, or other available adjuvants or combinations of adjuvants. Freund's complete adjuvant is not generally used clinically for human vaccines. A pharmaceutically acceptable carrier should also be included in the vaccine. Such carriers are well known to one skilled in the art and include, for example, liposomes or saline solution.

The vaccine preferably contains from about 0.2 to 5 mg in a one ml dose of BVp42.

The vaccine can be administered in one or more doses, the amount administered being adjusted to correspond with the number of innoculations, either together or over a period of time. Administration can be carried out conventionally, preferably parenterally.

The present invention is further described in the examples below. The examples are for illustration purposes, and are not intended to limit the scope of the invention.

EXAMPLES

Example I

Production and Purification of Baculovirus p42 (BVp42)

The Uganda Palo Alto (FUP) *Plasmodium falciparum* p42 coding region from $Ala_{1333}$ to $Ser_{1705}$ was cloned into a *Polyhedron californica* nuclear polyhedrosis virus (AcMNPV) polyhedrin promoter regulated expression system (26).

Figure 1B:
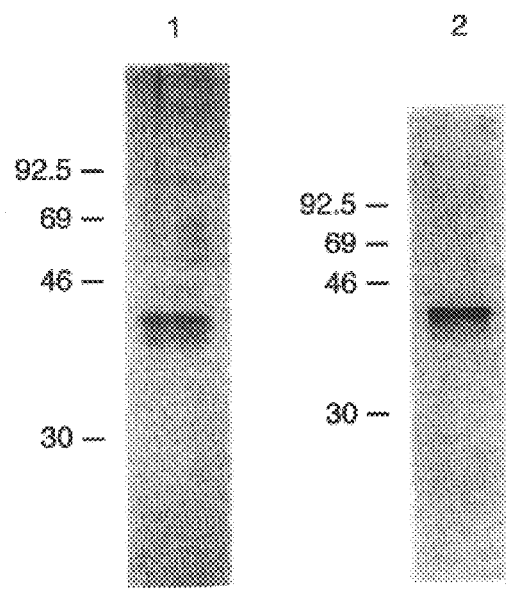

FIG. 1 shows, schematically, the sequences that were cloned into a BVp42 encoding shuttle vector. The coding sequence, shown at top, included the flg5 leader ($Flg_L$, solid box) fused to the FUP isolate p42 coding region from $Ala_{1333}$ to $Ser_{1705}$. The BamH1fragment finally obtained was cloned into a AcMNPV transfer plasmid, shown at the bottom of the figure. The leader sequence for flg5 has been shown to direct secretion of the mature flg5 protein (27). When fused to p42 coding DNA in the baculovirus expression system, the mature protein is also found to be secreted from the insect cells. "RV" is an EcoRV restriction site. The construct was made as follows.

Oligomers encoding the flg5 leader (27), 5' portion of FUP isolate p42 from $Ala_{1333}$ to the HindIII site at amino acid $Arg_{1362}$ and BamH1 sites were made on an automated DNA synthesizer (Applied Biosystems, Foster City, Calif.), kinased, annealed, and ligated. The overlapping oligomers consisted of six 43-mers, two 46-mers and two 19-mers. After digestion with BamH1, the ligation product was ligated into BamH1-digested and phosphatased pAB114, a HindIII/Sa1 deletion of pBR322 containing a BamH1 linker (30). The HindIII/Sal1 fragment of p42 from a pAB125 ADH$_2$-GAPDH α-factor construct (32), which includes an in-frame stop codon following $Ser_{1705}$, was ligated in-frame into this pAB114 vector to yield a flg5 leader fused to full-length p42 flanked by unique BamH1 sites. The BamH1 fragment was subsequently cloned into the BamH1 site of the AcMNPV transfer plasmid pAc373 (26). The recombinant shuttle vector obtained was then used to transfer the coding sequence into AcMNPV by homologous recombination through transfection of sf9 cells (24). Recombinant viruses were initially identified visually by occlusion negative phenotype and plaque hybridization with the BamH1 fragment labeled by the oligomer primed extension method (31). The recombinant AcMNPV expression vector obtained, Flg5LFUP42AcNPV, was deposited with the American Type Culture Collection, 12301 Parklawn Drive, Rockville, Md. 20852, U.S.A. on Jan. 28, 1992 and has been assigned accession number VR2354. Infection of sf9 cells was carried out conventionally per Summers and Smith (24).

Protein expression was initially monitored in roller bottles. Production was then scaled up to 0.5 liter batches in 2.8 liter Fernbach shaker flasks. Culture supernatants were concentrated 10 to 50-fold by tangential flow ultrafiltration (Amicon). Recombinant BVp42 was purified from the concentrated supernatant by the affinity chromatography technique utilized to purify parasite gp195 as described by Siddiqui et al. (7) (summarized below in Example III).

FIG. 2A shows silver stains (lane 1) and immunoblots (lane 2) of the affinity chromatography purified BVp42. The silver stained antigens were electrophoresed in SDS polyacrylamide gels. The immunoblots were reacted with a rabbit anti-parasite gp195 serum pool.

A single band migrating at approximately 44 kDa was observed in the silver stain. In the immunoblots, the purified BVp42 displayed major immunoreactive species at the positions of the major protein bands, accompanied by minor reactivities with proteins of higher and lower molecular weight.

The DNA sequence of the BVp42 construct from BamHI to SalI is shown in FIG. 7, the numbering starting with the first nucleotide of BamHI and ending with the last nucleotide of SalI. A restriction map is shown schematically at the top of the figure and the same sites are shown adjacent to the corresponding sequences below.

Example II

Production and Purification of Yeast p42 (Yp42)

A yeast p42 construct used in the Examples was expressed in the alcohol dehydrogenase 2/glyceraldehyde-3-phosphate dehydrogenase ($ADH_2$-GAPDH) regulated expression system of *Saccharomyces cerevisiae* and has been described fully in Hui et al. 1991, incorporated by reference (32). The p42 construct was based on the gp195 coding region from $Ala_{1333}$ to $Ser_{1705}$ of the FUP isolate (SEQ ID NO: 2) (33). The yeast p42 polypeptide (Yp42) was purified using an affinity chromatography technique described by Siddiqui et al. 1987 for the purification of parasite gp195 (7) (summarized below), except that polyclonal rabbit anti-gp195 IgG was used for antigen purification instead of anti-gp195 monoclonal antibody 5.2, because the Yp42 protein could not be recovered in significant amounts using this monoclonal antibody.

FIG. 2B shows silver stains (lane 1) and immunoblots (lane 2) of the affinity chromatography purified Yp42. The silver stained antigens were electrophoresed in SDS polyacrylamide gels. The Immunoblots were reacted with a rabbit anti-parasite gp195 serum pool.

In the silver stain, a major species corresponding to Yp42 migrated as a 44 kDa molecule, although other minor bands were also present in varying amounts. In the immunoblots, the purified Yp42 displayed major immunoreactive species at the positions of the major protein bands, accompanied by minor reactivities with proteins of higher and lower molecular weight.

Example III

Isolation of Purified, Parasite gp195 with Selected Fragments that Can Induce Substantially Complete Protection Against *Plasmodiusn falciparum* Challenge A mixture of gp195 protein and certain of its processing fragments was obtained from in vitro cultured parasites (*P. falciparum* Uganda Palo Alto strain) using monoclonal-antibody affinity chromatography procedures employing Nab 5.2(7); i.e. the mixture is enriched in the epitope for which Mab 5.2 is specific. Importantly, this mixture has been previously shown to be capable of inducing substantially complete protection against a homologous challenge of *Plasmodium falciparum* in Aotus monkeys (7). References in the examples below to "gp195" refer to the Mab 5.2-purified mixture of gp195 enriched with certain of its processing fragments.

In summary, saponin-lysed parasites were extracted with 1% NP-40 and the lysate was clarified by ultracentrifugation. The extracts were passed through a Protein G Sepharose column covalently conjugated with gp195-specific monoclonal antibody Mab 5.2 (described in U.S. Pat. No. 4,897,354, incorporated by reference herein, and deposited with the American Type Culture Collection, 12301 Parklawn Dr., Rockville, MD. 20852, U.S.A. on Jul. 17, 1986 under accession number HB 9148). Mab 5.2 is specific for an antigenic determinant contained in p42, as demonstrated below.

After extensive washing to remove non-specifically bound material, specifically-bound proteins were eluted with 0.1 M glycine (pH 2.5) and neutralized with 1 M Tris-HCl (pH 8.0). The purity of the isolated gp1 95 was examined by SDS-PAGE followed by silver staining.

Example IV

In vitro Inhibition Assay

Substantially complete parasite inhibition was found obtainable using BVp42 as an immunogen in in vitro parasite growth inhibition assays. This level of inhibition has only observed by us to be induced by the Mab 5.2 affinity-purified mixture of gp195 and fragments (8).

In vitro parasite growth inhibition assays were performed by culturing parasites in the presence of immune rabbit serum using established methods (8). Briefly, parasites were cultured in the presence of 15% preimmune serum or immune rabbit serum obtained 14, 21, 28, and 35 days after the fourth immunization with BVp42 in Complete Freund's Adjuvant (indicated as 4D14, 4D21, 4D28 and 4D35 in Table I below). The starting parasitemia (S) in each of the experiments was 0.2%. Growth inhibition was calculated according to the following equation:

$$\% \text{ inhibition} = \frac{(P-S)-(T-S)}{(P-S)} \times 100\%, \text{ where}$$

$P$ = % parasitemia of cultures containing 15% preimmune serum at 72 hours, $T$ = % parasitemia of cultures containing 15% immune serum at 72 hours, and $S$ = starting % parasitemia of cultures at 0 hours Quaternary sera were used in inhibition assays. The corresponding pre-immune serum of each animal was used as a control. Parasite cultures were synchronized by sorbitol lysis (34) to select for late trophozoite and schizont stages. Infected erythrocytes were adjusted to an initial parasitemia of approximately 0.2% and a hematocrit of 0.8% with fresh erythrocytes. Rabbit preimmune or immune serum was added to a final concentration of 15%, and 200 ul of the culture suspension was added in duplicate wells to a 96-well microtiter plate. Cultures were incubated at 37° C. for 72 hours, and the parasitemia was determined by microscopy. The experiment was repeated three times for each of the rabbits used (rabbit given identification nos. 131 and 132). Results are shown in Table I.

TABLE I

In Vitro Parasite Growth Inhibition Assay with Rabbit Anti-BVp42 Sera

| Rabbit Serum | % Parasitemia (% Inhibition) | | |
|---|---|---|---|
| | Expt. 1 | Expt. 2 | Expt. 3 |
| Anti-BVp42 (131): | | | |
| Preimmune | 13.3 | 6.8 | 9.8 |
| 4D14 | 10.3 (23) | — | — |
| 4D21 | 5.6 (58) | 3.9 (44) | 4.0 (60) |
| 4D28 | — | 1.7 (77) | 2.6 (75) |
| 4D35 | — | 1.6 (79) | 1.9 (82) |
| Anti-BVp42 (132): | | | |
| Preimmune | 9.0 (11) | 6.7 | 8.7 |
| 4D14 | 5.4 (47) | — | — |
| 4D21 | <0.1 (>99) | 0.4 (98) | 0.2 (100) |
| 4D28 | — | 0.3 (98) | 0.3 (99) |
| 4D35 | — | 0.3 (98) | 0.9 (92) |

Quaternary sera of rabbits immunized with Yp42 had no significant effect on in vitro parasite growth (data not shown). In contrast, significant inhibition was obtained with quaternary sera of several bleeding dates from both rabbits immunized with BVp42 (Table I). Sera obtained from later bleedings of rabbit 132 (4D21, 4D28, 4D35) nearly completely inhibited parasite growth; similar levels of inhibition have been observed previously only with antisera against mAb 5.2 purified, parasite gp195 (8).

Example V

Determination of Immunogenicities and Cross-reactivities of Recombinant Polypeptides A. ELISA Titers of Rabbits Immunized with Purified Parasite gp195 Against gp195, BVp42 and Yeast p42.

Rabbits were immunized with BVp42, Yp42 or enriched gp195 mixture (i.e. enriched for gp195 and C-terminal containing processing fragments through Mab 5.2 affinity purification) to determine the immunogenicity of the recombinant polypeptides and the cross-reactivity of anti-recombinant p42 antibodies with native gp195.

Rabbits given identification nos. 103, 104, 106 and 115 were immunized with purified, parasite gp195 emulsified in Complete Freund's Adjuvant as described (8). Rabbits 131 and 132 were immunized intramuscularly four times at 21-day intervals with 50 ug of purified BVp42 in Complete Freund's Adjuvant. Rabbits 93 and 96 were immunized intramuscularly five times at 21-day intervals with 50 ug of purified Yp42 in Complete Freund's Adjuvant. The amount of mycobacteria was reduced to one half of the first dose for the second immunization and one fourth of the first dose for subsequent immunizations, with the volume being replaced with Incomplete Freund's Adjuvant. Rabbits were bled before immunization and weekly after each immunization.

Serum antibodies produced against enriched gp195 mixture, BVp42, or Yp42 were assayed by an enzyme-linked immunosorbent assay (23, 33) using the following technique.

Vinyl plates were coated with purified, parasite gp195 and fragments (0.08 ug/ml), recombinant BVp42 (0.08 ug/ml), or recombinant Yp42 (0.2 ug/ml) and washed and blocked with 1% bovine serum albumin in borate buffered saline (BBS: 167 mM borate/134 mM NaCl, pH 8.0). Rabbit and mouse sera were serially diluted in 1% BSA/BBS, and human sera were serially diluted in phosphate-buffered saline (PBS: 150 mM sodium phosphate, 500 mM NaCl, pH 7.4) containing 0.05% Tween 20, 1.5% powdered milk, 0.05% BSA and 0.05% thimerosal. Diluted sera were added to antigen-coated wells and incubated for 1 hr at room temperature. Plates were washed with BBS containing 0.5 M NaCl (HSBBS) (rabbit and mouse sera) or PBS with 0.05% Tween 20 (human sera), and an appropriate dilution of peroxidase-conjugated species-specific anti-IgG (heavy and light chain specific) was added and incubated for 1 hr (anti-rabbit and anti-mouse IgG) or 2 hrs (anti-human IgG) at room temperature. Plates were washed in HSBBS and finally in BBS. One hundred microliters of peroxidase substrate solution [$H_2O_2$ and 2,240 -azino-bis(3-ethylbenzothiazoline-6-sulfonate)] were added to each well, and the absorbance value at 410 nm was determined with a Dynatech 605 ELISA reader. The endpoint of ELISA titers for rabbit sera was designated to be the serum dilution producing an absorbance value of 0.2, which corresponded to twice the background O.D. reading. The ELISA endpoint titers for human sera was designated to be the serum dilution producing an absorbance value greater than 0.056, which was two standard deviations above the average reading for normal human sera.

A comparison of the reactivity of the polyclonal antisera from rabbits immunized with the purified, enriched parasite gp195, BVp42, and Yp42 in an ELISA is shown in Table II.

TABLE II

ELISA Titers of Rabbits Immunized with Purified, Parasite Gp195 Against Parasite Gp195, Baculovirus p42, and Yeast p42

| Rabbit Serum | Gp195 Titer | BVp42 Titer | Yp42 Titer |
|---|---|---|---|
| 103 | 1/140,000 | 1/5,400 | 1/1,000 |
| 104 | 1/300,000 | 1/7,000 | 1/1,300 |
| 106 | 1/330,000 | 1/20,000 | 1/3,000 |
| 115 | 1/160,000 | 1/4,200 | 1/800 |

The highest ELISA titers were obtained against parasite gp195, the immunogen, with lower titers against BVp42, and the lowest titers against Yp42. These results are consistent with the expectation that antibodies are induced by gp195 outside of the p42 fragment, leading to a higher titer against the gp195 preparation than against BVp42.

B. ELISA and IFA Titers of Rabbits Immunized with BVp42 and Yeast p42 Against Parasite gp195, BVp42 and Yp42.

Additional rabbits were immunized with purified BVp42 (nos. 131,132) or purified Yp42 (nos. 93,96) to determine the immunogenicity of the recombinant polypeptides and the cross-reactivity of anti-recombinant p42 antibodies with native gp195. Rabbit sera were tested by ELISA, parasite indirect immunofluorescence (IFA), and immunoblotting with parasite gp195.

The IFA procedure used was as follows. Assays were performed on acetone-fixed thin blood smears of schizonts and merozoites as described (35). Endpoint IFA titers corresponded to the final serum dilution producing parasite immunofluorescence above background levels observed using preimmune rabbit sera.

Sera were obtained on the day indicated (day 14, 21, 28 or 35, indicated as 4D14, etc. in Table III below) after four immunizations of rabbits with 50 ug BVp42 or 50 ug Yp42. Serial dilutions of sera were titered for reactivity with plates coated with recombinant p42 (rp42) or parasite gp195. "rp42" corresponds to BVp42 for rabbit anti-BVp42 sera and Yp42 for rabbit anti-Yp42 sera. The method of determining the ELISA endpoint titer for rabbit sera was as discussed above. Endpoint IFA titers correspond to the final serum dilution producing parasite immunofluorescence above preimmune serum backgrounds.

BVp42 proved to be highly immunogenic as shown in Table III, inducing antibody titers comparable to those of rabbits immunized with purified, parasite gp195 (Table II).

TABLE III

ELISA and IFA Titers of Rabbits Immunized with Baculovirus p42 and Yeast p42 Against Parasite Gp195, Baculovirus p42 and Yeast p42

| Rabbit Serum | rp42 ELTSA Titer | Gp195 ELISA Titer | IFA Titer |
|---|---|---|---|
| Anti-BVp42 (131): | | | |
| 4D21 | 1/100,000 | 1/30,000 | 1/25,600 |
| 4D28 | 1/120,000 | 1/130,000 | 1/51,200 |
| 4D35 | 1/98,000 | 1/160,000 | 1/204,800 |
| Anti-Bvp42 (132): | | | |
| 4D21 | 1/74,000 | 1/85,000 | 1/51,200 |
| 4D28 | 1/120,000 | 1/300,000 | 1/102,400 |
| 4D35 | 1/88,000 | 1/300,000 | 1/204,800 |
| Anti-Yp42 (93): | | | |
| 4D14 | 1/60,000 | 1/2,000 | 1/1,600 |
| 4D21 | 1/40,000 | 1/2,000 | 1/3,200 |
| 4D28 | 1/50,000 | 1/3,000 | 1/6,400 |
| Anti-Yp42 (96) | | | |
| 4D14 | 1/25,000 | 1/900 | 1/800 |
| 4D21 | 1/23,000 | 1/800 | 1/3,200 |
| 4D28 | 1/30,000 | 1/700 | 1/6,400 |

As shown in Table III, ELISA titers were similar in assays utilizing plates coated with either purified, parasite gp195 or BVp42. Very high ELISA titers were obtained late in the quaternary response (days 28 and 35). Yp42 was less immunogenic than BVp42, inducing lower antibody titers against the immunogen. In addition, the cross-reactivity of anti-Yp42 antibodies with parasite gp195 in the ELISA was much lower than the cross-reactivity of anti-BVp42 antibodies. Typical merozoite surface staining patterns were observed by IFA for the BVp42 antisera (data not shown), and IFA titers obtained after the fourth immunization (Table III) reached levels exceeding those obtained by immunization with purified, parasite gp1 95 (data not shown). Yp42 induced much lower IFA titers.

C. ELISA Inhibition Assay

In order to obtain an estimate of the degree of cross-reactivity of anti-parasite gp195 (enriched mixture) antibodies with BVp42 and Yp42, we performed an ELISA inhibition assay utilizing the various antigens as inhibitors. The ELISA inhibition assay measures the reduction in reactivity of anti-parasite gp195 sera with parasite gp195 antigen in the presence of various concentrations of soluble parasite gp195 or recombinant p42. The ELISA inhibition assay was performed by diluting rabbit antisera to a point on the descending portion of the ELISA titration curve. The diluted sera (rabbit anti-parasite gp195 sera 103, 104, 106, and 115) were mixed with various concentrations of inhibitor (gp1 95, BVp42 or Yp42), incubated for 1 hour, and added to purified, parasite gp195-coated plates. Subsequent steps in the ELISA inhibition assay were identical to the standard ELISA assay described in section A above.

The results are shown in FIG. 4. Soluble parasite gp195 completely inhibited the binding of anti-gp195 sera in this assay. A high level of inhibition (82–92%) was also obtained with soluble BVp42. Much lower levels of inhibition were seen with soluble Yp42 (28–47%). The average antigen concentration required to obtain 50% inhibition in the ELISA was similar for parasite gp195 (0.03 ug/ml) and BVp42 (0.04 ug/ml), while >5 ug/ml Yp42 was required for 50% inhibition. These results suggest that a majority of antibodies against parasite gp195 also recognize BVp42, i.e. purified, parasite gp195 and BVp42 are highly cross-reactive.

D. Reactivity with Human Sera

The recognition of gp195 (without Mab 5.2 affinity purified fragments) and related recombinant polypeptides by serum antibodies of individuals from a malaria-endemic area of the Philippines have been analyzed by Kramer and Oberst. Several individuals from this study were examined for antibody reactivity with parasite gp195 (Mab 5.2 affinity purified), BVp42 and Yp42. The results are shown in Table IV.

TABLE IV

Reactivity of Human Sara from a Malaria-Endemic Area with Purified, Parasite Gp195, the Baculovirus p42 Polypeptide, and the Yeast p42 Polypeptide

| Individual | Gp195 ELISA Titer | BVp42 ELISA Titer | Yp42 ELISA Titer |
|---|---|---|---|
| 14270 | 1/100 | 1/200 | neg. |
| 14103 | 1/102,400 | 1/51,200 | 1/400 |
| 14122 | 1/102,400 | 1/51,200 | 1/400 |
| 14184 | 1/3,200 | 1/3,200 | 1/800 |
| 13563 | 1/200 | 1/1,600 | neg. |
| 13691 | 1/51,200 | 1/12,800 | 1/200 |
| 14187 | 1/21,800 | 1/12,800 | 1/100 |

Serial serum dilutions were tested for reactivity with the plates coated with parasite gp195, BVp42 and Yp42. Endpoint titers were designated as the serum dilution producing an O.D.>0.056, which was two standard deviations above the average reading for normal human sera. There was an excellent correlation between ELISA titers obtained with parasite gp195 and BVp42 (Pearson's correlation coefficient r=0.96, p<.001). A lower correlation was obtained for gp195 and Yp42 ELISA titers (Pearson's correlation coefficient r=0.86, p<.01). Thus, BVp42 cross reacts with serum antibodies of humans from the malaria endemic area of the Philippines.

E. Recognition of Conformational Determinants by Antibodies of Rabbits Immunized with Parasite gp195 and Recombinant p42 and by a gp195 specific monoclonal antibody (Mab 5.2).

FIG. 3, Panels A and B show immunoblots of purified parasite gp195 electrophoresed under nonreducing (panel A) or reducing (panel B) conditions in a 11.5% SDS-polyacrylamide gel. Immunoblots were reacted with the following antibody preparations: lane 1, anti-gp195 monoclonal antibody 5.2; lane 2, rabbit anti-parasite gp195; lane 3, rabbit anti-BVp42 (#131); lane 4, rabbit anti-BVp42 (#32); lane 5, rabbit anti-Yp42 (#93); lane 6, rabbit anti-Yp42 (#96). Panel C: Immunoblots of Bvp42 (lane 1, non-reduced; lane 2, reduced) and Yp42 (lane 3, non-reduced; lane 4, reduced) reacted with Mab 5.2.

The procedure for immunoblotting was as follows. Purified gp195 and BVp42 polypeptides were dissolved in Laemmli's buffer with or without 2-mercaptoethanol as a reducing agent and separated on NaDodSO$_4$ polyacrylamide gels (36). The separated proteins were electrophoretically transferred to nitrocellulose (37) and reacted with rabbit and mouse antisera as described by Chang et al., 1989 (23).

FIGS. 3A & B, lane 1, show that Mab 5.2 is specific for a conformational determinant of the p42 fragment of gp195 since reactivity with this antibody was diminished by reduction of the parasite antigen.

FIG. 3, (FIG. 3B lanes 2, 3 and 4) also demonstrates that reactivity with the p42 processing fragments of both anti-gp195 sera and anti-BVp42 sera was markedly decreased when parasite gp195 was electrophoresed under reducing conditions. This indicates that both these antisera primarily recognize disulfide, conformational determinants of parasite gp195. In contrast, reactivity of anti-Yp42 sera, as shown in FIG. 3B (lanes 5 and 6) was slightly enhanced for reduced gp195, and the reduced 19 kDa processing fragment was recognized by these sera. Thus, the anti-Yp42 appears to recognize gp195 epitopes that are not disulfide-dependent.

The strong reactivity of BVp42 with monoclonal antibody 5.2, as shown in FIG. 3C, lane 1, and the loss of this reactivity by reduction of BVp42, as shown in FIG. 3C, lane 2, indicates that the conformation of BVp42 closely resembles that of the native protein.

Example VI

Recognition of BVp42 by Antibodies From Congenic Mouse Strains

It has previously been shown that responsiveness to purified, parasite gp195 is present in mice of diverse major histocompatibility complex makeup (23). We determined whether the BVp42 antigen would be similarly recognized by anti-gp195 antibodies from a panel of congenic mouse strains.

Sera of seven congenic mouse strains possessing different H-2 haplotypes on the B10 background and immunized with purified, parasite gp195 were tested for reactivity with the BVp42 antigen (FIG. 5). Congenic mice of the following strain designations differing in H-2 haplotype but sharing the C57BL/10 genetic background were immunized: C57BL/10 SnJ, B10.A/SgSnJ, B10.D2/nSnJ, B10.M/SN, B10.WB (69NS), B10.BR/SgSnJ, and B10.PL (Jackson Laboratories, Bar Harbor, Me.). Five mice per group were immunized intraperitoneally four times at 2-week intervals with 5 µg of purified, parasite gp195 emulsified in Complete Freund's Adjuvant. Mice were bled before immunization, on days 7 and 10 after the first immunization and on days 5, 7,and 14 after subsequent immunizations.

All seven strains produced anti-gp195 antibodies recognizing epitopes of BVp42 with some variation in titer among strains. Thus, similar to parasite gp195, individuals of diverse MHC haplotypes are capable of producing antibodies recognizing BVp42.

Example VII

Reactivity of BVp42 With Homologous vs. Heterologous Antigens

Since the gp42 processing fragment contains both conserved and allelic determinants, the reactivity of anti-BVp42 antibodies with homologous vs. heterologous gp195 antigens was characterized. Four parasite isolates, FUP, FVO, Hond-1 and Pf857 were used and Southern blot analyses with allele specific oligonucleotide probes showed that FUP and Pf857 belong to the MAD allele, and FVO and Hond-1 belong to the K1 allele. Native gp195 antigens were purified by affinity chromatography from FUP and FVO parasites. In ELISAs, identical titers and binding curves were obtained with anti-BVp42 antibodies using either FUP (homologous) or FVO (heterologous) gp195 as antigens. Similar results were obtained in indirect immunofluorescent assays with FVO and FUP merozoites. More importantly, anti-BVp42 antibodies strongly or completely inhibited the in vitro parasite growth of the heterologous parasites (FVO and Hond-1) to the same degree as with the homologous parasites (FUP and Pf857).

References

All patents, publications and patent applications referred to herein are hereby incorporated by reference.

1. Holder, A. A. and R. R. Freeman. 1981. Immunization against blood-stage rodent malaria using purified parasite antigens. *Nature* 294:361.
2. Majarian, W. R., T. M. Daly, W. P. Weidanz and C. A. Long. 1984. Passive immunization against murine malaria with an IgG3 monoclonal antibody. *J. Immunol.* 132:3131.
3. Lew, A. M., C. J. Langford, R. F. Anders, D. J. Kemp, A. Saul, C. Fardoulys and M. Sheppard. 1989. A protective monoclonal antibody recognizes a linear epitope in the precursor of the major merozoite antigens of *Plasmodium chabaudi adami*. *Proc. Natl. Acad. Sci. USA* 86:3768.
4. Hall, R., J. E. Hyde, M. Goman, D. L. Simmons, I. A. Hope, M. Mackay, J. Scaife, B. Merkli, R. Richle and J. Stocker. 1984. Major surface antigen gene of a human malaria parasite cloned and expressed in bacteria. *Nature* 311:379.
5. Perrin, L. H., B. Merkli, M. Loche, C. Chizzolini, J. Smart and R. Richle. 1984. Antimalarial immunity in Saimiri monkeys. Immunization with surface components of asexual blood stages. *J. Exp. Med.* 160:441.
6. Patarroyo, M. E., P. Romero, M. L. Torres, P. Clavijo, D. Andreu, D. Lozada, L. Sanchez, P. del Portillo, C. Pinilla, A. Moreno, A. Alegria and R. Houghten. 1987. Protective synthetic peptides against experimental *Plasmodium falciparum*-induced malaria. In Vaccines 87. F. Brown, R. Chanock, and R. Lerner, editors. Cold Spring Harbor Laboratory Press, Cold Spring Harbor, New York. 117–124.
7. Siddiqui, W. A., L. Q. Tam, K. J. Kramer, G. S. N. Hui, S. E. Case, K. M. Yamaga, S. P. Chang, E. B. T. Chan and S-C. Kan. 1987. Merozoite surface coat precursor protein completely protects Aotus monkeys against *Plasmodium falciparum* malaria. *Proc. Natl. Acad. USA*. 84:3014.
8. Hui, G. S. N. and W. A. Siddiqui. 1987. Serum from Pf195 protected Aotus monkeys inhibits *Plasmodium falciparum* growth in vitro. *Exp. Parasitol.* 64:519
9. Cheung, A., J. Leban, A. R. Shaw, B. Merkli, J. Stocker, C. Chizzolini, C. Sander and L. H. Perrin. 1986. Immunization with synthetic peptides of a *Plasmodium falciparum* surface antigen induces antimerozoite antibodies. *Proc. Natl. Acad. Sci. USA* 83:8328.
10. Knapp, B., A. Shaw, E. Hundt, B. Enders and H. A. Kupper. 1988. A histidine alanine rich recombinant antigen protects Aotus monkeys from *P. falciparum* infection. *Behring Inst. Mitt.* 82:349.
11. Herrera, S., M. A. Herrera, B. L. Perlaza, Y. Burki, P. Caspers, H. Dobeli, D. Rotmann and U. Certa. 1990. Immunization of Aotus monkeys with *Plasmodium falciparum* blood-stage recombinant proteins. *Proc. Natl. Acad. Sci. USA* 87:4017.
12. Holder, A. A., R. R. Freeman and S. C. Nicholls. 1988. Immunization against *Plasmodium falciparum* with recombinant polypeptides produced in *Escherichia coli*. *Parasite Immunol.* 10:607.
13. Tanabe, K., M. Mackay, M. Goman, and J. Scaife. 1987. Allelic Dimorphism in a Surface Antigen of the Malaria Parasite *Plasmodium falciparum*. *J. Mol. Biol.* 195:273

14. Patarroyo, M. E., P. Romero, M. L. Torres, P. Clavijo, A. Moreno, A. Martinez, R. Rodriguez, F. Guzman and E. Cabezas. 1987. Induction of protective immunity against experimental infection with malaria using synthetic peptides. *Nature* 328:629.
15. Rodriguez, R., A. Moreno, F. Guzman, M. Calvo and M. E. Patarroyo. 1990. Studies in owl monkeys leading to the development of a synthetic vaccine against the asexual blood stages of *Plasmodium falciparum*. *Am. J. Trop. Med. Hyg.* 43:339.
16. Patarroyo, M. E., R. Amador, P. Clavijo, A. Moreno, F. Guzman, P. Romero, R. Tascon, A. Franco, L. A. Murillo, G. Ponton and G. Trujillo. 1988. A synthetic vaccine protects humans against challenge with asexual blood stages of *Plasmodium falciparum* malaria. *Nature* 332:158.
17. Ruebush, T. K., G. H. Campbell, A. Moreno, M. E. Patarroyo and W. E. Collins. 1990. Immunization of owl monkeys with a combination of *Plasmodium falciparum* a sexual blood-stage synthetic pepide antigens. *Am. J. Trop. Med. Hyg.* 43:355–366.
18. Herrera, S., M. Herrera, F. Rosero, A. Corredor, C. Clavijo, U. Certa, and R. Guerrero. 1991. Assessment of *P. falciparum* malaria vaccine candidates in Aotus monkeys. Abstract in the IV International Congress on Malaria and Babesiosis.
19. Holder, A. A., Lockyer, M. J., Odink, K. C., Sandhu, J. S., Riveros-Moreno, V., Nicholls, S. C., Hillman, Y., Davey, L. S., Tizard, M. L. V., Schwarz, R. T. and R. R. Freeman. 1985. Primary structure of the precursor to the three major surface antigens of *Plasmodium falciparum* merozoites. *Nature* 317:270–273.
20. Mackay, M., Goman, M., Bone, N., Hyde, J. E., Scaife, J., Certa, U., Stunnenberg, H. and H. Bujard. 1985. Polymorphism of the precursor for the major surface antigens of *Plasmodium falciparum* merozoites: studies at the genetic level. *EMBO J.* 4:3823–3829.
21. Pirson, P. and M. Perkins. 1985. Characterization with monoclonal antibodies of a surface antigen of Plasmodium falciparum merozoites. *J. Immunol.* 134:1946.
22. Blackman, M. J., H-G. Heidrich, S. Donachie, J. S. McBride and A. A. Holder. 1990. A single fragment of a malaria merozoite surface protein remains on the parasite during red cell invasion and is the target of invasion-inhibiting antibodies. *J. Exp. Med.* 172:379.
23. Chang, S. P., G. S. N. Hui, A. Kato and W. A. Siddiqui. 1989. Generalized immunological recognition of the major merozoite surface antigen (gp195) of *Plasmodium falciparum*. *Proc. Natl. Acad. Sci. USA* 86:6343.
24. Summers, M. D. and G. E. Smith. 1986. A Manual of Methods for Baculovirus Vectors and Insect Culture Procedures, *Texas Agricultural Experimental Station Bull.* No. 1555, College Station, Tex.
25. Luckow, V. A. 1991. in Prokop et al., Cloning and Expression of Heterologous Genes in Insect Cells with Baculovirus Vectors, *Recombinant DNA Technology and Applications*, 97–152.
26. Luckow, V. A., M. D. Summers. 1988. Trends in the Development of Baculovirus Expression Vectors, *Biotechnology*, 6:47.
27. Kiefer, M. C., A. Baird, T. Nguyen, C. George-Nascimento, O. B. Mason, L. J. Boley, P. Valenzuela and P. J. Barr. 1991. Molecular cloning of a human basic fibroblast growth factor receptor cDNA and expression of a biologically active extracellular domain in a baculovirus system. *Growth Factors,* 5:115–127.
28. Hui, G. S. N, S. P. Chang, L. Q. Tam, A. Kato S. E. Case, C. Hashiro and W. A. Siddiqui. 1990. Characterization of Antibody Responses Induced by Different Synthetic Adjuvants to the *Plasmodium falciparum* Major Merozoite Surface Precursor Protein, gp195. *Vaccine 90 Cold Spring Harbor Laboratory Press.* 477–483.
29. Hui, G. S. N., L. Q. Tam, S. P. Chang, S. E. Case, C. Hashiro, W. A. Siddiqui, T. Shiba, S. Kusumoto and S. Kotani. 1991. Synthetic Low-Toxicity Muramyl Dipeptide and Monophosphoryl Lipid A Replace Freund Complete Adjuvant in Inducing Growth-Inhibitory Antibodies to the *Plasmodium falciparum* Major Merozoite Surface Protein, gp195. *Infection and Immunity.* 59:1585–1591.
30. Barr, P. J., L. S. Cousens, C. T. Lee-Ng, A. Medina-Selby, F. R. Masiarz, R. A. Hallewell, S. H. Chamberlain, J. D. Bradley, D. Lee, K. S. Steimer, L. Poulter, A. L. Burlingame, F. Esch and A. Baird. 1988. Expression and processing of biologically active fibroblast growth factors in the yeast *Saccharomyces cerevisiae*. *J. Biol. Chem.* 263:16471.
31. Feinberg, A. and B. Volgelstein. 1984. A technique for radio-labeling DNA restriction endonuclease fragments to high specific activity. *Anal. Biochem.* 137:266.
32. Hui, G. S. N., S. P. Chang, H. Gibson, A. Hashimoto, C. Hashiro, P. J. Barr, and S. Kotani. 1991. Influence of adjuvants on the antibody specificity to the *Plasmodium falciparum* major merozoite surface protein, gp195. *J. Immunol.,* 147:3935–3941.
33. Chang, S. P., K. J. Kramer, K. M. Yamaga, A. Kato, S. E. Case and W. A. Siddiqui, 1988. *Plasmodium falciparum*: Gene structure and hydropathy profile of the major merozoite surface antigen (gp195) of the Uganda-Palo Alto isolate. *Exp. Parasitol.* 67:1.
34. Lambros, C. and J. P. Vanderberg. 1979. Synchronization of *Plasmodium falciparum* erythrocytic stages in culture. *J. Parasitol.* 65:418.
35. Siddiqui, W. A., L. Tam, S.-C. Kan, K. J. Kramer, S. E. Case, K. L. Palmer, K. M. Yamaga and G. S. N. Hui. 1986. Induction of protective immunity to monoclonal-antibody-defined *Plasmodium falciparum* antigens requires a strong adjuvant in Aotus monkeys. *Infect. Immun.* 52:314.
36. Laemmli, U. K. 1970. Cleavage of structural proteins during the assembly of the head of bacteriophage T4. *Nature* 227:680.
37. Towbin, H., T. Staehelin, and J. Gordon. 1979. Electrophoretic transfer of proteins from polyacrylamide gels to nitrocellulose sheets: Procedure and some applications. *Proc. Natl. Acad. Sci. USA* 76:4350.

What is claimed is:

1. A composition comprising a polypeptide expressed by an insect cell which contains a baculovirus vector that encodes said polypeptide, wherein said polypeptide consists of a fragment of surface protein gp195 from *Plasmiodium falciparum*, said fragment consisting of an amino acid sequence selected from the group consisting of:
    (a) amino acids 1 to 373 of the amino acid sequence of SEQ ID NO:2;
    (b) amino acids 1 to 354 of the amino acid sequence of SEQ ID NO:3;
    (c) amino acids 1 to 373 of the amino acid sequence of SEQ ID NO:4; and
    (d) amino acids 1 to 356 of the amino acid sequence of SEQ ID NO:5,
wherein the amino acid sequence of (a), (b), (c) or (d) of said polypeptide is more immunogenic in a mammalian host than is a polypeptide having the same amino acid sequence expressed in yeast.

2. The composition of claim 1 which further comprises a pharmaceutically acceptable carrier.

3. The composition of claim 1, wherein the insect cells in which said polypeptide is expressed are selected from the group consisting of *Spodoptera frugiperda, Spodoptera exiaua, Choristoneura fumiferana, Trichoplusia ni* and *Spodoptera littoralis*.

4. The composition of claim 1 which further comprises an adjuvant.

5. The composition of claim 4, wherein said adjuvant is selected from the group consisting of Freund's complete adjuvant, Freund's incomplete adjuvant, B30-MDP, LA-15-PH, saponin, aluminum hydroxide and combinations thereof.

6. The composition of claim 1 which comprises from 0.2 to 5 mg of said polypeptide.

7. A composition comprising a polypeptide expressed by insect cells which contain a baculovirus vector that encodes said polypeptide, wherein said polypeptide consists of a fragment of surface protein gp95 from *Plasmodium falciparum*, said fragment consisting of an amino acid sequence selected from the group consisting of:

(a) amino acids 1 to 394 of the amino acid sequence of SEQ ID NO:2;

(b) amino acids 1 to 375 of the amino acid sequence of SEQ ID NO:3;

(c) amino acids 1 to 394 of the amino acid sequence of SEQ ID NO:4; and (d) amino acids 1 to 377 of the amino acid sequence of SEQ ID NO:5, wherein the amino acid sequence of (a), (b), (c) or (d) of said polypeptide is more immunogenic in a mammalian host than is a polypeptide having the same amino acid sequence expressed in yeast.

8. The composition of claim 7 which further comprises a pharmaceutically acceptable carrier.

9. The composition of claim 7, wherein the insect cells in which said polypeptide is expressed are selected from the group consisting of *Spodoptera frugiperda, Spodoptera exiaua, Choristoneura fumiferana, Trichoplusia ni* and *Spodoptera littoralis*.

10. The composition of claim 7 which further comprises an adjuvant.

11. The composition of claim 10, wherein said adjuvant is selected from the group consisting of Freund's complete adjuvant, Freund's incomplete adjuvant, B30-MDP, LA-15-PH, saponin, aluminum hydroxide and combinations thereof.

12. The composition of claim 7 which comprises from 0.2 to 5 mg of said polypeptide.

13. A composition comprising a polypeptide expressed by an insect cell which contains a baculovirus vector that encodes said polypeptide, wherein said polypeptide comprises a fragment of surface protein gp195 from *Plasmodium falciparum*, said fragment consisting of an amino acid sequence selected from the group consisting of:

(a) amino acids 1 to 394 of the amino acid sequence of SEQ ID NO:2;

(b) amino acids 1 to 375 ofthe amino acid sequence of SEQ ID NO:3;

(c) amino acids 1 to 394 of the amino acid sequence of SEQ ID NO:4;

(d) amino acids 1 to 377 of the amino acid sequence of SEQ ID NO:5;

(e) amino acids 1 to 373 of the amino acid sequence of SEQ ID NO:2;

(f) amino acids 1 to 354 of the amino acid sequence of SEQ ID NO:3;

(g) amino acids 1 to 373 of the amino acid sequence of SEQ ID NO;4; and (h) amino acids 1 to 356 of the amino acid sequence of SEQ ID NO:5, wherein the amino acid sequence of (a), (b), (c), (d), (e), (f), (g) or (h) of said polypeptide is more immunogenic in a mammalian host than is a polypeptide having the same amino acid sequence expressed in yeast.

* * * * *

UNITED STATES PATENT AND TRADEMARK OFFICE
CERTIFICATE OF CORRECTION

PATENT NO. : 6,420,523 B1
DATED : July 16, 2002
INVENTOR(S) : Chang et al.

It is certified that error appears in the above-identified patent and that said Letters Patent is hereby corrected as shown below:

Title page,
Item [57], ABSTRACT,
Line 3, change "the" to -- that --.

Item [56], OTHER PUBLICATIONS,
"Holder et al., reference", change "boold" to -- blood --.
"Knapp et al., reference", change "histidin" to -- histidine --.
"Lew et al., reference", change "merozite" to -- merozoite --.
"Ruebish et al., reference", change "Oql" to -- Owl --.
"Holder et al., reference", change "*Plasmosium*" to -- *Plasmodium* --.
"Holder et al., reference", change "presursor" to -- precursor --.

Column 1,
Line 44, delete "a".
Line 49, change "parasite mias" to -- parasitemais --.

Column 4,
Line 14, change "sf9" to -- Sf9 --.
Line 18, after "the" (first instance), insert -- MAD isolate --.
Line 18, after "Wellcome isolate," insert -- (SEQ ID NO:5) --.
Line 28, change "(SEQ ID NO:5)" to -- (SEQ ID NO:3) --.
Line 48, change "gp1 95" to -- gp195 --.
Line 56, delete "is".

Column 5,
Line 28, change "gp1 195" to -- gp195 --.
Line 45, change "promotor" to -- promoter --.
Line 49, change "promotor" to -- promoter --.
Line 55, change "viruses," to -- virus, --.
Line 56, change "*Polyhedron*" to -- *Autographa* --.

Column 6,
Line 24, change "sf," to -- Sf9, --.
Line 42, change "sf" to -- Sf9 --.
Line 49, change "*Polyhedron*" to -- *Autographa* --.
Line 53, change "*trichoplusia*" to -- *Tricholplusia* --.

UNITED STATES PATENT AND TRADEMARK OFFICE
CERTIFICATE OF CORRECTION

PATENT NO. : 6,420,523 B1
DATED : July 16, 2002
INVENTOR(S) : Chang et al.

It is certified that error appears in the above-identified patent and that said Letters Patent is hereby corrected as shown below:

Column 7,
Line 21, change "sf9" -- Sf9 --.

Column 8,
Line 13, change "*Polyhedron*" to -- *Autographa* --.
Line 20, change "BamH1fragment" to -- BamH1 fragment --.
Line 46, change "sf9" to -- Sf9 --.
Line 54, change "sf9" to -- Sf9 --.

Column 9,
Line 38, change "Immunoblots" to -- immunoblots --.
Line 58, change "Nab" to -- Mab --.

Column 11,
Line 44, change "p42" to -- p42 --.

Column 12,
Line 14, change "2,240 -azino" to -- 2,2'-azino --.
Line 17, change "605" to -- 605 --.

Column 14,
Line 10, change "without" to -- with --.

Signed and Sealed this

Twenty-fifth Day of February, 2003

JAMES E. ROGAN
*Director of the United States Patent and Trademark Office*

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 1219 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmodium falciparum
        (B) STRAIN: falciparum uganda palo alto (vii) IMMEDIATE SOURCE:
        (B) CLONE: flg5LFUP42AcNPV (ix) FEATURE:
        (A) NAME/KEY: exon
        (B) LOCATION: 13..1194

(xi) SEQUENCE DESCRIPTION: SEQ ID NO:1:

```
GGATCCACTG GGATGTGGAG CTGGAAGTGC CTCCTCTTCT GGGCTGTCCT GGTCACAGCC      60
ACACTCTGCA CCGCGGCGAT ATCTGTCACA ATGGATAATA TCCTCTCAGG ATTTGAAAAT     120
GAATATGATG TTATATATTT AAAACCTTTA GCTGGAGTAT ATAGAAGCTT AAAAAAACAA     180
ATTGAAAAAA ACATTTTTAC ATTTAATTTA AATTTGAACG ATATCTTAAA TTCACGTCTT     240
AAGAAACGAA ATATTTCTT AGATGTATTA GAATCTGATT TAATGCAATT TAAACATATA      300
TCCTCAAATG AATACATTAT TGAAGATTCA TTTAAATTAT TGAATTCAGA ACAAAAAAAC     360
ACACTTTTAA AAAGTTACAA ATATATAAAA GAATCAGTAG AAAATGATAT TAAATTTGCA     420
CAGGAAGGTA TAAGTTATTA TGAAAAGGTT TTAGCGAAAT ATAAGGATGA TTTAGAATCA     480
ATTAAAAAAG TTATCAAAGA AGAAAAGGAG AAGTTCCCAT CATCACCACC AACAACACCT     540
CCGTCACCAG CAAAAACAGA CGAACAAAAG AAGGAAAGTA AGTTCCTTCC ATTTTTAACA     600
AACATTGAGA CCTTATACAA TAACTTAGTT AATAAAATTG ACGATTACTT AATTAACTTA     660
AAGGCAAAGA TTAACGATTG TAATGTTGAA AAAGATGAAG CACATGTTAA AATAACTAAA     720
CTTAGTGATT TAAAAGCAAT TGATGACAAA ATAGATCTTT TTAAAAACCA TAACGACTTC     780
GAAGCAATTA AAAAATTGAT AAATGATGAT ACGAAAAAAG ATATGCTTGG CAAATTACTT     840
AGTACAGGAT TAGTTCAAAA TTTTCCTAAT ACAATAATAT CAAAATTAAT TGAAGGAAAA     900
TTCCAAGATA TGTTAAACAT TTCACAACAC CAATGCGTAA AAAAACAATG TCCAGAAAAT     960
TCTGGATGTT TCAGACATTT AGATGAAAGA GAAGAATGTA AATGTTTATT AAATTACAAA    1020
CAAGAAGGTG ATAAATGTGT TGAAAATCCA AATCCTACTT GTAACGAAAA TAATGGTGGA    1080
TGTGATGCAG ATGCCAAATG TACCGAAGAA GATTCAGGTA GCAACGGAAA GAAAATCACA    1140
TGTGAATGTA CTAAACCTGA TTCTTATCCA CTTTTCGATG GTATTTTCTG CAGTTAGTAG    1200
TCGACCCTTG GAAGGATCC                                                 1219
```

(2) INFORMATION FOR SEQ ID NO:2:

(i) SEQUENCE CHARACTERISTICS:
        (A) LENGTH: 394 amino acids
        (B) TYPE: amino acid
        (C) STRANDEDNESS: single
        (D) TOPOLOGY: linear -continued (ii) MOLECULE TYPE: peptide (iii) HYPOTHETICAL: NO (iv) ANTI-SENSE: NO (v) FRAGMENT TYPE: C-terminal (vi) ORIGINAL SOURCE:
    (A) ORGANISM: Plasmodium falciparum
    (B) STRAIN: falciparum uganda palo alto (FUP)

(xi) SEQUENCE DESCRIPTION: SEQ ID NO:2:

```
Ala Ile Ser Val Thr Met Asp Asn Ile Leu Ser Gly Phe Glu Asn  Glu
1               5                   10                  15

Tyr Asp Val Ile Tyr Leu Lys Pro Leu Ala Gly Val Tyr Arg Ser  Leu
            20                  25                  30

Lys Lys Gln Ile Glu Lys Asn Ile Phe Thr Phe Asn Leu Asn Leu  Asn
                35                  40                  45

Asp Ile Leu Asn Ser Arg Leu Lys Arg Lys Tyr Phe Leu Asp  Val
        50                  55                  60

Leu Glu Ser Asp Leu Met Gln Phe Lys His Ile Ser Ser Asn Glu  Tyr
65                  70                  75                  80

Ile Ile Glu Asp Ser Phe Lys Leu Leu Asn Ser Glu Gln Lys Asn  Thr
                85                  90                  95

Leu Leu Lys Ser Tyr Lys Tyr Ile Lys Glu Ser Val Glu Asn Asp  Ile
                100                 105                 110

Lys Phe Ala Gln Glu Gly Ile Ser Tyr Tyr Glu Lys Val Leu Ala  Lys
            115                 120                 125

Tyr Lys Asp Asp Leu Glu Ser Ile Lys Lys Val Ile Lys Glu Glu  Lys
130                 135                 140

Glu Lys Phe Pro Ser Ser Pro Pro Thr Thr Pro Pro Ser Pro Ala  Lys
145                 150                 155                 160

Thr Asp Glu Gln Lys Lys Glu Ser Lys Phe Leu Pro Phe Leu Thr  Asn
                165                 170                 175

Ile Glu Thr Leu Tyr Asn Asn Leu Val Asn Lys Ile Asp Asp Tyr  Leu
            180                 185                 190

Ile Asn Leu Lys Ala Lys Ile Asn Asp Cys Asn Val Glu Lys Asp  Glu
            195                 200                 205

Ala His Val Lys Ile Thr Lys Leu Ser Asp Leu Lys Ala Ile Asp  Asp
    210                 215                 220

Lys Ile Asp Leu Phe Lys Asn His Asn Asp Phe Glu Ala Ile Lys  Lys
225                 230                 235                 240

Leu Ile Asn Asp Asp Thr Lys Lys Asp Met Leu Gly Lys Leu Leu  Ser
                245                 250                 255

Thr Gly Leu Val Gln Asn Phe Pro Asn Thr Ile Ile Ser Lys Leu  Ile
            260                 265                 270

Glu Gly Lys Phe Gln Asp Met Leu Asn Ile Ser Gln His Gln Cys  Val
            275                 280                 285

Lys Lys Gln Cys Pro Glu Asn Ser Gly Cys Phe Arg His Leu Asp  Glu
    290                 295                 300

Arg Glu Glu Cys Lys Cys Leu Leu Asn Tyr Lys Gln Glu Gly Asp  Lys
305                 310                 315                 320

Cys Val Glu Asn Pro Asn Pro Thr Cys Asn Glu Asn Asn Gly Gly  Cys
                325                 330                 335

Asp Ala Asp Ala Lys Cys Thr Glu Glu Asp Ser Gly Ser Asn Gly  Lys
                340                 345                 350
```

```
Lys Ile Thr Cys Glu Cys Thr Lys Pro Asp Ser Tyr Pro Leu Phe Asp
        355                 360                 365

Gly Ile Phe Cys Ser Ser Asn Phe Leu Gly Ile Ser Phe Leu Leu
        370                 375                 380

Ile Leu Met Leu Ile Leu Tyr Ser Phe Ile
385                 390
```

(2) INFORMATION FOR SEQ ID NO:3:

(i) SEQUENCE CHARACTERISTICS:
        (A) LENGTH: 375 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (vi) ORIGINAL SOURCE:
        (A) ORGANISM: Plasmodium falciparum
        (B) STRAIN: K1

(xi) SEQUENCE DESCRIPTION: SEQ ID NO:3:

```
Ala Val Thr Pro Ser Val Ile His Asn Ile Leu Ser Lys Ile Glu Asn
1               5                   10                  15

Glu Tyr Glu Val Leu Tyr Leu Lys Pro Leu Ala Gly Val Tyr Arg Ser
                20                  25                  30

Leu Lys Lys Gln Leu Glu Asn Asn Val Met Thr Phe Asn Val Asn Val
        35                  40                  45

Lys Asp Ile Leu Asn Ser Pro Phe Asn Lys Arg Glu Asn Phe Lys Asn
    50                  55                  60

Val Leu Glu Ser Asp Leu Ile Pro Tyr Lys Asp Leu Thr Ser Ser Asn
65                  70                  75                  80

Tyr Val Val Lys Asp Pro Tyr Leu Phe Leu Asn Lys Glu Lys Arg Asp
                85                  90                  95

Lys Phe Leu Ser Ser Tyr Asn Tyr Ile Lys Asp Ser Ile Asp Thr Asp
                100                 105                 110

Ile Asn Phe Ala Asn Asp Val Leu Gly Tyr Tyr Lys Ile Leu Ser Glu
        115                 120                 125

Lys Tyr Lys Ser Asp Leu Asp Ser Ile Lys Tyr Ile Asn Asp Lys
        130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
                165                 170                 175

Glu Ala Lys Val Leu Asn Tyr Thr Tyr Glu Lys Ser Asn Val Glu Ile
                180                 185                 190

Lys Glu Leu Ile Tyr Leu Lys Thr Ile Gln Asp Lys Leu Ala Asp Phe
                195                 200                 205

Lys Lys Asn Asn Asn Phe Val Gly Ile Ala Asp Leu Ser Thr Asp Tyr
        210                 215                 220

Asn His Asn Asn Leu Leu Thr Lys Phe Leu Ser Thr Gly Met Val Phe
225                 230                 235                 240

Glu Asn Leu Leu Lys Ser Ile Leu Ser Asn Leu Leu Asp Trp Lys Leu
                245                 250                 255
```

```
Ala Arg Tyr Val Lys His Phe Thr Thr Pro Met Arg Lys Lys Thr Met
            260                 265                 270

Ile Gln Gln Asn Ser Gly Cys Phe Arg His Leu Asp Glu Arg Glu Glu
            275                 280                 285

Cys Lys Cys Leu Leu Asn Tyr Lys Gln Glu Gly Ser Lys Cys Val Glu
            290                 295                 300

Asn Pro Asn Pro Thr Cys Asn Glu Asn Gly Gly Cys Asp Ala Asp
305             310                 315                 320

Ala Lys Cys Thr Glu Glu Asp Ser Gly Ser Asn Gly Lys Lys Ile Thr
            325                 330                 335

Cys Gln Cys Thr Lys Pro Asp Ser Tyr Pro Leu Ser Met Val Ile Phe
            340                 345                 350

Cys Ser Ser Asn Phe Leu Gly Ile Ser Phe Leu Leu Ile Leu Met
            355                 360                 365

Leu Ile Leu Tyr Ser Phe Ile
            370                 375
```

(2) INFORMATION FOR SEQ ID NO:4:

(i) SEQUENCE CHARACTERISTICS:
        (A) LENGTH: 394 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (vi) ORIGINAL SOURCE:
        (A) ORGANISM: Plasmodium falciparum
        (B) STRAIN: MAD (xi) SEQUENCE DESCRIPTION: SEQ ID NO:4:

```
Ala Ile Ser Val Thr Met Asp Asn Ile Leu Ser Gly Phe Glu Asn Glu
1               5                   10                  15

Tyr Asp Val Ile Tyr Leu Lys Pro Leu Ala Gly Val Tyr Arg Ser Leu
            20                  25                  30

Lys Lys Gln Ile Glu Lys Asn Ile Ile Thr Phe Asn Leu Asn Leu Asn
            35                  40                  45

Asp Ile Leu Asn Ser Arg Leu Lys Lys Arg Lys Tyr Phe Leu Asp Val
50                  55                  60

Leu Glu Ser Asp Leu Met Gln Phe Lys His Ile Ser Ser Asn Glu Tyr
65              70                  75                  80

Ile Ile Glu Asp Ser Phe Lys Leu Leu Asn Ser Glu Gln Lys Asn Ile
                85                  90                  95

Leu Leu Lys Ser Tyr Lys Tyr Ile Lys Glu Ser Val Glu Asn Asp Ile
            100                 105                 110

Lys Phe Ala Gln Glu Gly Ile Ser Tyr Tyr Glu Lys Val Leu Ala Lys
            115                 120                 125

Tyr Lys Asp Asp Leu Glu Ser Ile Lys Val Ile Lys Glu Glu Lys
            130                 135                 140

Glu Lys Phe Pro Ser Ser Pro Thr Thr Pro Ser Pro Ala Lys
145             150                 155                 160

Thr Asp Glu Gln Lys Lys Glu Ser Lys Phe Leu Pro Phe Leu Thr Asn
            165                 170                 175

Ile Glu Thr Leu Tyr Asn Asn Leu Val Asn Lys Ile Asp Asp Tyr Leu
```

-continued

```
                180                 185                 190
Ile Asn Leu Lys Ala Lys Ile Asn Asp Cys Asn Val Glu Lys Asp  Glu
            195                 200                 205
Ala His Val Lys Ile Thr Lys Leu Ser Asp Leu Lys Ala Ile Asp  Asp
            210                 215                 220
Lys Ile Asp Leu Phe Lys Asn Thr Asn Asp Phe Glu Ala Ile Lys  Lys
225                 230                 235                 240
Leu Ile Asn Asp Asp Thr Lys Lys Asp Met Leu Gly Lys Leu Leu  Ser
                245                 250                 255
Thr Gly Leu Val Gln Ile Phe Pro Asn Thr Ile Ile Ser Lys Leu  Ile
                260                 265                 270
Glu Gly Lys Phe Gln Asp Met Leu Asn Ile Ser Gln His Gln Cys  Val
            275                 280                 285
Lys Lys Gln Cys Pro Glu Asn Ser Gly Cys Phe Arg His Leu Asp   Glu
290                 295                 300
Arg Glu Glu Cys Lys Cys Leu Leu Asn Tyr Lys Gln Glu Gly Asp  Lys
305                 310                 315                 320
Cys Glu Glu Asn Pro Asn Pro Thr Cys Asn Glu Asn Asn Gly Gly  Cys
                325                 330                 335
Asp Ala Asp Ala Thr Cys Thr Glu Glu Asp Ser Gly Ser Ser Arg  Lys
            340                 345                 350
Lys Ile Thr Cys Glu Cys Thr Lys Pro Asp Ser Tyr Pro Leu Phe  Asp
            355                 360                 365
Gly Ile Phe Cys Ser Ser Ser Asn Phe Leu Gly Ile Ser Phe Leu  Leu
            370                 375                 380
Ile Leu Met Leu Ile Leu Tyr Ser Phe Ile
385                 390
```

(2) INFORMATION FOR SEQ ID NO:5:

(i) SEQUENCE CHARACTERISTICS:
        (A) LENGTH: 377 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (vi) ORIGINAL SOURCE:
        (A) ORGANISM: Plasmodium falciparum
        (B) STRAIN: WEL (xi) SEQUENCE DESCRIPTION: SEQ ID NO:5:

```
Ala Val Thr Thr Ser Val Ile Asp Asn Ile Leu Ser Lys Ile Glu  Asn
1               5                   10                  15
Glu Tyr Glu Val Leu Tyr Leu Lys Pro Leu Ala Gly Val Tyr Arg  Ser
                20                  25                  30
Leu Lys Lys Gln Leu Glu Asn Asn Val Met Thr Phe Asn Val Asn  Val
            35                  40                  45
Lys Asp Ile Leu Asn Ser Arg Phe Asn Lys Arg Glu Asn Phe Lys  Asn
50                  55                  60
Val Leu Glu Ser Asp Leu Ile Pro Tyr Lys Asp Leu Thr Ser Ser  Asn
65                  70                  75                  80
Tyr Val Val Lys Asp Pro Tyr Lys Phe Leu Asn Lys Glu Lys Arg  Asp
                85                  90                  95
```

-continued

```
Lys Phe Leu Ser Ser Tyr Asn Tyr Ile Lys Asp Ser Ile Asp Thr Asp
            100                 105                 110

Ile Asn Phe Ala Asn Asp Val Leu Gly Tyr Tyr Lys Ile Leu Ser Glu
            115                 120                 125

Lys Tyr Lys Ser Asp Leu Asp Ser Ile Lys Lys Tyr Ile Asn Asp Lys
            130                 135                 140

Gln Gly Glu Asn Glu Lys Tyr Leu Pro Phe Leu Asn Asn Ile Glu Thr
145                 150                 155                 160

Leu Tyr Lys Thr Val Asn Asp Lys Ile Asp Leu Phe Val Ile His Leu
            165                 170                 175

Glu Ala Lys Val Leu Asn Tyr Thr Tyr Glu Lys Ser Asn Val Glu Val
            180                 185                 190

Lys Ile Lys Glu Leu Asn Tyr Leu Lys Thr Ile Gln Asp Lys Leu Ala
            195                 200                 205

Asp Phe Lys Lys Asn Asn Asn Phe Val Gly Ile Ala Asp Leu Ser Thr
210                 215                 220

Asp Tyr Asn His Asn Asn Leu Leu Thr Lys Phe Leu Ser Thr Gly Met
225                 230                 235                 240

Val Phe Glu Asn Leu Leu Lys Ser Val Leu Ser Asn Leu Leu Asp Trp
            245                 250                 255

Lys Leu Ala Arg Tyr Val Lys His Phe Thr Thr Pro Met Arg Lys Lys
            260                 265                 270

Thr Met Ile Gln Gln Ser Ser Gly Cys Phe Arg His Leu Asp Glu Arg
            275                 280                 285

Glu Glu Cys Lys Cys Leu Leu Asn Tyr Lys Gln Glu Gly Asp Lys Cys
            290                 295                 300

Val Glu Asn Pro Asn Pro Thr Cys Asn Glu Asn Asn Gly Gly Cys Asp
305                 310                 315                 320

Ala Asp Ala Lys Cys Thr Glu Glu Asp Ser Gly Ser Asn Gly Lys Lys
            325                 330                 335

Ile Thr Cys Glu Cys Thr Lys Pro Asp Cys Tyr Pro Leu Phe Asp Gly
            340                 345                 350

Ile Phe Cys Ser Ser Ser Asn Phe Leu Gly Ile Ser Phe Leu Leu Ile
            355                 360                 365

Leu Met Leu Ile Leu Tyr Ser Phe Ile
370                 375
```